(12) United States Patent
Hoffmann

(10) Patent No.: US 8,734,368 B2
(45) Date of Patent: *May 27, 2014

(54) PERCUSSION ASSISTED ANGIOGENESIS

(75) Inventor: Andrew Kenneth Hoffmann, Burnaby (CA)

(73) Assignee: Simon Fraser University, Burnaby (CA)

(*) Notice: Subject to any disclaimer, the term of this patent is extended or adjusted under 35 U.S.C. 154(b) by 1719 days.

This patent is subject to a terminal disclaimer.

(21) Appl. No.: 12/218,054

(22) Filed: Jul. 11, 2008

(65) Prior Publication Data

US 2008/0275343 A1 Nov. 6, 2008

Related U.S. Application Data

(63) Continuation of application No. 11/036,386, filed on Jan. 18, 2005, now abandoned, which is a continuation-in-part of application No. 10/902,122, filed on Jul. 30, 2004, now Pat. No. 7,517,328.

(30) Foreign Application Priority Data

Sep. 4, 2003 (CA) .................................. 2439667

(51) Int. Cl.
*A61H 1/00* (2006.01)
*A61H 1/02* (2006.01)
*A61H 5/00* (2006.01)
(52) U.S. Cl.
USPC .............................................. 601/2; 600/439
(58) Field of Classification Search
USPC ............................................. 600/439; 601/2
See application file for complete search history.

(56) References Cited

U.S. PATENT DOCUMENTS 827,133 A 7/1906 Weston
1,498,680 A 6/1924 Clement et al.
(Continued)

FOREIGN PATENT DOCUMENTS

BG 49287 10/1991
EP 429 109 5/1991
(Continued)

OTHER PUBLICATIONS

Matsuda, T et al, Extracorporeal Cardiac Shock Wave Therapy Markedly Ameliorates Ischemia-Induced Myocardial Dysfunction in Pigs In Vivo, Circulation 2004; 110; 3055-3061.

(Continued)

*Primary Examiner* — James Kish
(74) *Attorney, Agent, or Firm* — IProperty Inc.; Laurence C. Bonar; Graeme A. Herring

(57) ABSTRACT

The present invention relates to a new non-invasive method for inducing angiogenesis and more particularly coronary angiogenesis wherein an operator applies localized percussion upon the upper torso proximate an ischemic myocardial region, whereby the percussive forces penetrate to cause sheer stresses to the endothelium of the coronaries which lie thereupon, and thereby cause new coronary growth by virtue of endogenous liberation of beneficial angiogenic mediators. A pair of vibratory contacts are advantageously applied to rib-spaces to either side of the sternum (or alternatively to the upper back), where-after percussion is applied at the resonance frequency of the heart/epimyocardium at a displacement amplitude of 0.1 mm-15 mm (preferably greater than 1 mm), such as to maximize an internal oscillatory effect. The system is also adaptable for cerebral and peripheral vasculature applications. Ultrasonic imaging may optionally be utilized to direct percussive therapy.

25 Claims, 6 Drawing Sheets

(56) References Cited

U.S. PATENT DOCUMENTS

| | | | |
|---|---|---|---|
| 2,181,282 A | 11/1939 | Oster | |
| 2,821,191 A | 1/1958 | Paii | |
| 3,085,568 A | 4/1963 | Whitesell | |
| 3,352,303 A | 11/1967 | Delaney | |
| 3,499,436 A | 3/1970 | Balamuth | |
| 3,664,331 A | 5/1972 | Filipovici | |
| 3,735,755 A | 5/1973 | Eggleton et al. | |
| 3,779,249 A | 12/1973 | Semler | |
| 3,853,121 A | 12/1974 | Mizrachy et al. | |
| 4,079,733 A | 3/1978 | Denton et al. | |
| 4,098,266 A | 7/1978 | Muchisky et al. | |
| 4,216,766 A | 8/1980 | Duykers et al. | |
| 4,232,661 A | 11/1980 | Christensen | |
| 4,269,175 A | 5/1981 | Dillon | |
| RE31,603 E | 6/1984 | Christensen | |
| 4,484,569 A | 11/1984 | Driller et al. | |
| 4,507,816 A | 4/1985 | Smith et al. | |
| 4,538,596 A | 9/1985 | Colasante | |
| 4,651,716 A | 3/1987 | Forester et al. | |
| 4,779,615 A | 10/1988 | Frazier et al. | |
| 4,785,797 A | 11/1988 | Cuervo | |
| 4,791,915 A | 12/1988 | Barsotti et al. | |
| 4,838,263 A | 6/1989 | Warwick et al. | |
| 4,932,414 A | 6/1990 | Coleman et al. | |
| 4,955,365 A | 9/1990 | Fry et al. | |
| 4,966,131 A | 10/1990 | Houghton et al. | |
| 5,005,579 A | 4/1991 | Wurster et al. | |
| 5,040,537 A | 8/1991 | Katakura | |
| 5,065,741 A | 11/1991 | Uchiyama et al. | |
| 5,101,810 A | 4/1992 | Skille et al. | |
| 5,107,837 A | 4/1992 | Ophir et al. | |
| 5,132,942 A | 7/1992 | Cassone | |
| 5,143,070 A | 9/1992 | Ophir et al. | |
| 5,143,073 A | 9/1992 | Dory | |
| 5,150,712 A | 9/1992 | Dory | |
| 5,159,838 A | 11/1992 | Lynnworth | |
| 5,172,692 A | 12/1992 | Kulow et al. | |
| 5,178,147 A | 1/1993 | Ophir et al. | |
| 5,190,766 A | 3/1993 | Ishihara | |
| 5,197,946 A | 3/1993 | Tachibana | |
| 5,207,214 A | 5/1993 | Romano | |
| 5,230,334 A | 7/1993 | Klopotek et al. | |
| 5,243,997 A | 9/1993 | Uflacker et al. | |
| 5,247,937 A | 9/1993 | Ophir et al. | |
| 5,267,223 A | 11/1993 | Flanagan et al. | |
| 5,291,894 A | 3/1994 | Nagy | |
| 5,293,870 A | 3/1994 | Ophir et al. | |
| 5,303,433 A | 4/1994 | Jang | |
| 5,307,816 A | 5/1994 | Hashimoto et al. | |
| 5,391,140 A | 2/1995 | Schaetzle et al. | |
| 5,413,550 A | 5/1995 | Castel | |
| 5,423,862 A | 6/1995 | Clarke et al. | |
| 5,442,710 A | 8/1995 | Komatsu | |
| 5,453,081 A | 9/1995 | Hansen | |
| 5,454,373 A | 10/1995 | Koger et al. | |
| 5,474,070 A | 12/1995 | Ophir et al. | |
| 5,509,896 A | 4/1996 | Carter | |
| 5,520,612 A | 5/1996 | Winder et al. | |
| 5,520,614 A | 5/1996 | McNamara et al. | |
| 5,523,058 A | 6/1996 | Umemura et al. | |
| 5,524,620 A | 6/1996 | Rosenschein | |
| 5,549,119 A | 8/1996 | Solar | |
| 5,555,891 A | 9/1996 | Eisenfeld | |
| 5,556,372 A | 9/1996 | Talish et al. | |
| 5,558,092 A | 9/1996 | Unger et al. | |
| 5,569,170 A | 10/1996 | Hansen | |
| 5,586,346 A | 12/1996 | Stacy et al. | |
| 5,606,754 A | 3/1997 | Hand et al. | |
| 5,613,940 A | 3/1997 | Romano | |
| 5,626,554 A | 5/1997 | Ryaby et al. | |
| 5,674,262 A | 10/1997 | Tumey | |
| 5,676,637 A | 10/1997 | Lee | |
| 5,695,460 A | 12/1997 | Siegel et al. | |
| 5,698,531 A | 12/1997 | Nabel et al. | |
| 5,713,848 A | 2/1998 | Dubrul et al. | |
| 5,720,304 A | 2/1998 | Omura | |
| 5,725,482 A | 3/1998 | Bishop | |
| 5,728,123 A | 3/1998 | Lemelson et al. | |
| 5,762,616 A | 6/1998 | Talish | |
| 5,830,177 A | 11/1998 | Li et al. | |
| 5,861,015 A | 1/1999 | Benja-Athon | |
| 5,873,828 A | 2/1999 | Fujio et al. | |
| 5,879,314 A | 3/1999 | Peterson et al. | |
| 5,913,834 A | 6/1999 | Francais | |
| 5,919,139 A | 7/1999 | Lin | |
| 5,936,163 A | 8/1999 | Greathouse | |
| 5,951,501 A | 9/1999 | Griner | |
| 5,973,999 A | 10/1999 | Naff et al. | |
| 5,983,429 A | 11/1999 | Stacy et al. | |
| 6,027,444 A | 2/2000 | Franck | |
| 6,036,662 A | 3/2000 | Van Brunt et al. | |
| 6,068,596 A | 5/2000 | Weth et al. | |
| 6,082,365 A | 7/2000 | Yenin | |
| 6,093,164 A | 7/2000 | Davis et al. | |
| 6,095,979 A | 8/2000 | Ohtomo | |
| 6,110,098 A | 8/2000 | Renirie et al. | |
| 6,126,619 A | 10/2000 | Peterson et al. | |
| 6,146,342 A | 11/2000 | Glen | |
| 6,155,976 A | 12/2000 | Sackner et al. | |
| 6,193,677 B1 | 2/2001 | Cady | |
| 6,200,259 B1 | 3/2001 | March | |
| 6,254,573 B1 | 7/2001 | Haim et al. | |
| 6,261,537 B1 | 7/2001 | Klaveness et al. | |
| 6,270,459 B1 | 8/2001 | Ophir et al. | |
| 6,273,864 B1 * | 8/2001 | Duarte et al. | 601/2 |
| 6,277,085 B1 | 8/2001 | Flynn | |
| 6,283,935 B1 | 9/2001 | Laufer et al. | |
| 6,287,271 B1 | 9/2001 | Dubrul et al. | |
| 6,296,617 B1 | 10/2001 | Peeler et al. | |
| 6,330,475 B1 | 12/2001 | Renirie et al. | |
| 6,332,872 B1 | 12/2001 | Young | |
| 6,398,772 B1 | 6/2002 | Bond et al. | |
| 6,408,205 B1 | 6/2002 | Remirie et al. | |
| 6,424,864 B1 | 7/2002 | Matsuura | |
| 6,428,477 B1 | 8/2002 | Mason | |
| 6,432,070 B1 | 8/2002 | Talish et al. | |
| 6,432,072 B1 | 8/2002 | Harris et al. | |
| 6,434,539 B1 | 8/2002 | Woodsum et al. | |
| 6,471,663 B1 | 10/2002 | Van Brunt et al. | |
| 6,500,134 B1 | 12/2002 | Cassone | |
| 6,511,429 B1 | 1/2003 | Fatemi et al. | |
| 6,537,236 B2 | 3/2003 | Tucek et al. | |
| 6,540,700 B1 * | 4/2003 | Fujimoto et al. | 601/3 |
| 6,579,251 B1 | 6/2003 | Randoll | |
| 6,635,017 B1 | 10/2003 | Moehring et al. | |
| 6,682,496 B1 | 1/2004 | Pivaroff | |
| 6,687,625 B2 | 2/2004 | Ophire et al. | |
| 6,716,184 B2 | 4/2004 | Vaezy et al. | |
| 6,719,694 B2 | 4/2004 | Weng et al. | |
| 6,733,450 B1 | 5/2004 | Alexandrov et al. | |
| 6,936,025 B1 | 8/2005 | Evans et al. | |
| 7,090,300 B2 | 8/2006 | Fujita | |
| 7,229,423 B2 | 6/2007 | Horzewski | |
| 7,232,417 B2 | 6/2007 | Plante | |
| 7,789,841 B2 * | 9/2010 | Huckle et al. | 601/2 |
| 2001/0031922 A1 * | 10/2001 | Weng et al. | 600/439 |
| 2001/0051776 A1 * | 12/2001 | Lenhardt | 601/2 |
| 2002/0016560 A1 | 2/2002 | Hansen | |
| 2002/0049395 A1 | 4/2002 | Thompson et al. | |
| 2002/0055693 A1 | 5/2002 | Thompson et al. | |
| 2002/0072690 A1 | 6/2002 | Thompson et al. | |
| 2002/0072691 A1 | 6/2002 | Thompson et al. | |
| 2002/0082529 A1 | 6/2002 | Surosa et al. | |
| 2002/0091339 A1 | 7/2002 | Horzewski et al. | |
| 2002/0103454 A1 | 8/2002 | Sackner | |
| 2002/0193833 A1 | 12/2002 | Dimmer et al. | |
| 2003/0009119 A1 | 1/2003 | Kamm | |
| 2003/0028111 A1 | 2/2003 | Vaezy et al. | |
| 2003/0083599 A1 | 5/2003 | Kitov | |
| 2003/0135085 A1 | 7/2003 | Bassuk et al. | |
| 2003/0163067 A1 | 8/2003 | Lidgren | |
| 2003/0181812 A1 | 9/2003 | Rabiner et al. | |
| 2003/0204141 A1 | 10/2003 | Nock et al. | |
| 2003/0236476 A1 | 12/2003 | Inman et al. | |

(56) References Cited

U.S. PATENT DOCUMENTS

| | | |
|---|---|---|
| 2004/0006288 A1 | 1/2004 | Spector et al. |
| 2004/0122354 A1 | 6/2004 | Semba et al. |
| 2004/0133066 A1 | 7/2004 | Mann et al. |
| 2004/0153009 A1* | 8/2004 | Horzewski et al. ............ 601/2 |
| 2004/0173220 A1 | 9/2004 | Harry et al. |
| 2004/0267153 A1* | 12/2004 | Bergethon ................ 600/554 |
| 2005/0004460 A1 | 1/2005 | Taylor et al. |
| 2005/0096669 A1 | 5/2005 | Rabine et al. |
| 2005/0148807 A1 | 7/2005 | Salkinder |
| 2005/0203398 A1 | 9/2005 | Sandrin et al. |
| 2006/0282026 A1 | 12/2006 | Glen et al. |
| 2007/0123809 A1 | 5/2007 | Weiss et al. |
| 2007/0173751 A1 | 7/2007 | Ohashi |
| 2007/0225618 A1 | 9/2007 | Ward et al. |
| 2008/0221489 A1 | 9/2008 | Madsen et al. |

FOREIGN PATENT DOCUMENTS

| | | |
|---|---|---|
| FR | 608893 | 12/1925 |
| FR | 284 3290 | 2/2004 |
| GB | 2167961 | 6/1986 |
| JP | 4156823 | 5/1992 |
| JP | 8089549 | 4/1996 |
| JP | 11192276 | 7/1999 |
| RU | 2187295 C2 | 2/2002 |
| WO | WO 85/03634 | 8/1985 |
| WO | WO 87/05497 | 9/1987 |
| WO | WO 9428873 | 12/1994 |
| WO | WO 95/01770 | 1/1995 |
| WO | WO 96/39955 | 12/1996 |
| WO | WO 97/40806 | 11/1997 |
| WO | WO 00/00155 | 1/2000 |
| WO | WO 00/67693 | 11/2000 |
| WO | WO 02/04070 A1 | 1/2002 |
| WO | WO 02/07582 | 1/2002 |
| WO | WO 02/43645 | 6/2002 |
| WO | WO 02/054018 | 7/2002 |

OTHER PUBLICATIONS

Gutersohn, A et al,"Shock waves upregulate vascular endothelial growth factor m-RNA in human umbilical vascular endothelial cells." Circulation 2000; 102 (suppl): 18.
Fisher, AB et al, Endothelial cellular response to altered shear stress. Am J Physiol. 2001; 281;L529-L533.
Wang, CJ et al, "Shock wave-enhanced neovascularisation at the tendon-bone junction: an experiment in dogs." J Foot Ankle Surg. 2002;41:16-22.
Gutersohn, A et. al, "Non invasive Cardiac Angiogenesis shock wave therapy (NI-CATh) increased perfusion and exercise tolerance in endstage CAD patients." submitted WCC 2006.
Adams et al, "Periodic acceleration: effects on vasoactive, fibrinolytic, and coagulation factors." J Appl Physiol 98: 1083-1090, 2005.
Hudlicka, O et al, "Angiogenesls in skeletal and cardiac muscle." Physiol Rev 72: 369-417, 1992. pp. 377-378; 379-380; 383; 397-399; and 400-402.
Amaral S et al, "Angiotensin II and VEGF are Involved in angiogenesis Induced by short-term exercise training." Am J. Phys Heart Circ 281(3):H1163-H1169, Sep. 2001.
Suhr, "Effects of Short-term Vibration and Hypoxia during High-Intensity Cycling Exercise on Circulating Levels of Angiogenic Regulators in Humans"J App. Physiol Apr. 2007.
Malek et al, "Fluid shear stress differentially modulates expression of genes encoding basic fibroblast growth factor . . . " J Clin. Invest. 92: 2013-2021, 1993.
Mitsumata et al. "Fluid shear stress stimulates platelet-derived growth factor expression in endothelial cells." Am J. Physiol. 265 (1):H3-H8, Jul. 1993.
Sumpio "Hemodynamic forces and the biology of the endothelium: signal transduction pathways in endothelial cells subjected to physical forces," J Vasc Surg 13(5):744-6 May 91.

Ichioka et al "Effects of shear stress on wound-healing angiogenesis in the rabbit ear chamber." J of Surg. Res. 72:29-35, 1997.
Pipp, F et al "Elevated Fluid Shear Stress Enhances Postocclusive Collateral Artery Growth and Gene Expression in Pig Hind Limb." Art Thromb Vasc Biol 2004;24:1664.
Zou, J et al "Vibration induced hearing loss in guinea pig cochlea: expression of TNF-alpha and VEGF," Hearing Research vol. 202, Apr. 1-2, 2005, pp. 13-20.
Davies, P "Turbulent fluid shear stress induces vascular endothelial cell turnover in vitro." Proc. Natl. Acad. Sci. USA vol. 83, pp. 2114-2117, Apr. 1986 Cell Biology.
Krishan, L "Effect of mechanical boundary conditions on orientation of angiogenic microvessels." Cardiovasc. Research 2008 78(2):324-332.
Lacolley, "Mechanical influence of cyclic stretch on vascular endothelial cells," Card. Vasc. Research 64 (2004) 577-579.
Von Offenberg Sweeney et al, "Cyclic strain-mediated regulation of endothelial matrix metalloproteinase-2 expression and activity." Card Vasc Res. 2004 63(4): 625-634 Abstract.
Von Offenberg Sweeney et al,"Cyclic strain mediated regulation of vascular endothelial cell migration and tube formation." Bioch Biophys Res Comm 329(2) 2005 572-582 Abstract.
Wilson, E et al, "Mechanical Strain Induces Growth of Vascular Smooth Muscle Cells via Autocrine Action of PDGF." J Cell Bio. vol. 123, 1993 pp. 741-747.
Birnbaum, et al., "Ultrasound Has Synergistic Effects in Vitro with Tirofiban and Heparin for Thrombus Dissolution", *Thrombosis Research*, 96, (1999), pp. 451-458.
Birnbaum, et al., "Noninvasive In Vivo Clot Dissolution Without a Thrombolytic Drug—Recanalization of Thrombosed Iliofemoral Arteries by Transcutaneous Ultrasound Combined with Intravenous Infusion of Microbubbles", *Circulation* 1998, 97, pp. 130-134.
Birnbaum, et al., "Noninvasive Transthoracic Low Frequency Ultrasound Augments Thrombolysis in a Canine Model of Acute Myocardial Infarction—Evaluation of the Extent of ST-Segment Resolution", *Journal of Thrombosis and Thrombolysis* 11(3), pp. 229-234, 2001.
Blinc, et al., "Characterization of Ultrasound-Potentiated Fibrinolysis In Vitro", *Blood*, vol. 81, No. 10 (May 15, 1993), pp. 2636-2643.
Braaten, et al., "Ultrasound Reversibly Disaggregates Fibrin Fibers", *Thromb Haemost*, 1997, 78, pp. 1063-1068.
Christen, et al., "Effects of Intermittent Pneumatic Compression on Venous Haemodynamics and Fibrinolytic Activity", *Blood Coagulation and Fibrinolysis*, vol. 8, 1997, pp. 185-190.
Comerota, et al., "The Fibrinolytic Effects of Intermittent Pneumatic Compression", *Annals of Surgery*, vol. 226, No. 3, pp. 306-314, 1997.
Dalen, et al., "Coronary Spasm, Coronary Thrombosis, and Myocardial Infarction: A Hypothesis Concerning the Pathophysiology of Acute Myocardial Infarction", *American Heart Journal*, vol. 104, No. 5, Part 1, Nov. 1982, pp. 1119-1124.
Farber, et al., "Conduction of Cardiovascular Sound Along Arteries", *Circulation Research*, vol. XII, Mar. 1963, pp. 308-316.
Francis, et al., "Ultrasound Accelerates Transport of Recombinant Tissue Plasminogen Activator Into Clots", *Ultrasound in Med. & Biol.*, vol. 21, No. 3, pp. 419-424, 1995.
Francis, "Ultrasound-Enhanced Thrombolysis", *Echocardiography: A Jrnl. of CV Ultrasound & Allied Tech.*, vol. 18, No. 3, 2001, pp. 239-246.
Griesinger, et al., "Vibration Induced Current Fields and Cavitational Effect", *Zahnarztliche Praxis*, 1989, vol. 40, No. 6, pp. 213-217.
Hackett, et al., "Intermittent Coronary Occlusion in Acute Myocardial Infarction—Value of Combined Thrombolytic and Vasodilator Therapy", *The New England Journal of Medicine*, vol. 317, No. 17, pp. 1055-1059, 1987.
Honda, et al, "Mathematical Model of the Effects of Mechanical Vibration on Crossbridge Kinetics in Cardiac Muscle", *Jpn Circ J.*, 1994, 58: pp. 416-425.
Hudlicka, et al., "The Effect of Vibration on Blood Flow in Skeletal Muscle in the Rabbit", *Clinical Science and Molecular Medicine*, (1978), 55, pp. 471-476.

(56) References Cited

OTHER PUBLICATIONS

Jackson, et al., "Antithrombotic Therapy in Peripheral Arterial Occlusive Disease", *American College of Chest Physicians*, 2001, 119: pp. 283S-299S, http://www.chestjournal.org/cgi/content/full/119/1_suppl/283S.

Kasirajan, et al., "Management of Acute Lower Extremity Ischemia: Treatment Strategies and Outcome", *Current Interventional Cardiology Reports*, 2000, 2, pp. 119-129.

Koiwa, et al., "Measurement of Instantaneous Viscoelastic Properties by Impedance-Frequency Curve of the Ventricle", *Am. J. Physiol.*, 250, (Heart Circ. Physiol. 19), pp. H672-H684, 1986.

Koiwa, et al., "The Improvement of Systolic Function of Depressed Left Ventricle by External Vibration at Diastole", *Tohoku J. Exp. Med.*, 1989, 159, pp. 169-170.

Koiwa, et al., "Diastolic Vibration from the Precordium Increases Coronary Blood Flow in Humans", *J. Cardiovasc Diagn Procedures*, 1994, 12, p. 110, Abstract (FRI-POS 05).

Koiwa, et al., "The Effect of Diastolic Vibration on the Coronary Flow Rate in the Canine Heart With Ischemia", *J. Cardiovasc Diagn Procedures*, 1994, 12, p. 110, Abstract (FRI-POS 07).

Kovak, et al., "Thrombolysis Plus Aortic Counterpulsation: Improved Survival in Patients Who Present to Community Hospitals with Cardiogenic Shock", *J. Am. Coll. Cardiol.*, vol. 29, No. 7, Jun. 1997, pp. 1454-1458.

Lindblad, et al., "Effect of Vibration on a Canine Cutaneous Artery", *Am. J. Physiol.*, 250 (Heart Circ. Physiol. 19), pp. H519-H523, 1986.

Lincoff, et al., "Illusion of Reperfusion—Does Anyone Achieve Optimal Reperfusion During Acute Myocardial Infarction?", *Circulation*, Jun. 1993, 88, pp. 1361-1374.

Ljung, et al., "Inhibition of Vascular Smooth Muscle Contraction by Vibrations", *Abstract Acta Physiol. Scand.*, 396, Suppl., p. 95, 1973.

Ljung, et al., "Vibration-Induced Inhibition of Vascular Smooth Muscle Contraction", *Blood Vessels*, 12, pp. 38-52, 1975.

Luo, et al., "Enhancement of Thrombolysis in Vivo Without Skin and Soft Tissue Damage by Transcutaneous Ultrasound", *Thrombosis Research*, 89, 1998, pp. 171-177.

Luo, et al., "Transcutaneous Ultrasound Augments Lysis of Arterial Thrombi In Vivo", *Circulation*, vol. 94, No. 4, Aug. 1996, pp. 775-778.

Luo, et al., "Effect of External Ultrasound Frequency on Thrombus Disruption in Vitro", *Journal of Thrombosis and Thrombolysis*, 1996, 3, pp. 63-66.

Margulis, et al., "Physicochemical Processes Induced by Low-frequency Acoustic Vibrations in Liquids. I. Growth and Pulsation of Gas Bubbles", *Russian Journal of Physical Chemistry*, 56, 6, 1982, pp. 876-878.

Maseri, et al., "Coronary Vasospasm as a Possible Cause of Myocardial Infarction", *The New England Journal of Medicine*, vol. 299, No. 23, pp. 1271-1277, Dec. 1978.

Michalis, et al., "Vibrational Angioplasty and Hydrophilic Guidewires in the Treatment of Chronic Total Coronary Occlusions", *J. Endovasc. Ther.*, 2000, 7, pp. 141-148.

Morgan, et al., "Arterial Flow Enhancement by Impulse Compression", *Vasc. Surg.*, 25, pp. 8-16, Jan./Feb. 1991.

Nyborg, "Ultrasonic Microstreaming and Related Phenomena", *Br. J. Cancer*, 1982, 45, Suppl. V, 156, pp. 156-160.

Oliva, et al., "Arteriographic Evidence of Coronary Arterial Spasm in Acute Myocardial Infarction", *Circulation*, vol. 56, No. 3, Sep. 1977, pp. 366-374.

Olsson, et al., "Enhancement of Thrombolysis by Ultrasound", *Ultrasound in Med. & Biol.*, vol. 20, No. 4, pp. 375-382, 1994.

Ramcharan, et al., "The Effects of Vibration Upon Blood-Viscosity and Red-Cell Mobility: A Study of In Vivo and In Vitro", *Biorheology*, 19, pp. 341-352, 1982.

Riggs, et al., "Ultrasound Enhancement of Rabbit Femoral Artery Thrombolysis", *Cardiovascular Surgery*, vol. 5, No. 2, pp. 201-207, 1997.

Rosenschein, et al., "Experimental Ultrasonic Angioplasty: Disruption of Atherosclerotic Plaques and Thrombi in Vitro and Arterial Recanalization in Vivo", *J Am. Coll. Cardiol.*, vol. 15, No. 3, Mar. 1, 1990, pp. 711-717.

Rosenschein, et al., "Shock-Wave Thrombus Ablation, a New Method for Noninvasive Mechanical Thrombolysis", *The American Journal of Cardiology*, vol. 70, Nov. 15, 1992, pp. 1358-1361.

Sanborn, et al., "Impact of Thrombolysis, Intra-aortic Balloon Pump Counterpulsation, and Their Combination in Cardiogenic Shock Complicating Acute Myocardial Infarction: A Report from the SHOCK Trial Registry", *Journal of American College of Cardiology*, vol. 36, No. 3, Suppl. A., Sep. 2000, pp. 1123-1129.

Serikova, et al., "Effect of General Low-Frequency Vibration on the Functional State of the Blood", *Voenno-Meditsinskii Zhurnal*, 1977, pp. 59-62.

Siegel, et al., "Noninvasive, Transthoracic, Low-Frequency Ultrasound Augments Thrombolysis in a Canine Model of Acute Myocardial Infarction", *Circulation*, May 2, 2000, 101, pp. 2026-2029.

Siegel, et al., "Noninvasive Transcutaneous Low Frequency Ultrasound Enhances Thrombolysis in Peripheral and Coronary Arteries", *Echocardiography: A Jrnl. of CV Ultrasound & Allied Tech.*, vol. 18, No. 3, 2001, pp. 247-257.

Silver, et al., "The Relationship Between Acute Occlusive Coronary Thrombi and Myocardial Infarction Studied in 100 Consecutive Patients", *Circulation*, 61, No. 2, 1980, pp. 219-227.

Smith, et al., "Mechanical Vibration Transmission Characteristics of the Left Ventricle: Implications with Regard to Auscultation and Phonocardiography", *J. Am. Coll. Cardiol.*, vol. 4, No. 3, Sep. 1984, pp. 517-521.

Stone, et al., "Normal Flow (TIMI-3) Before Mechanical Reperfusion Therapy is an Independent Determinant of Survival in Acute Myocardial Infarction—Analysis from the Primary Angioplasty in Myocardial Infarction Trials", *Circulation*, Aug. 7, 2001, 104, pp. 636-641.

Suchkova, et al., "Enhancement of Fibrinolysis With 40-kHz Ultrasound", *Circulation*, 1998, 98, pp. 1030-1035.

Takagi, et al., "Diastolic Vibration Improves Systolic Function in Cases of Incomplete Relaxation", *Circulation*, vol. 86, No. 6, Dec. 1992, pp. 1955-1964.

Takashima, et al., "Effects of Mechanical Force on Blood Fibrinolytic Activity", *Thrombosis and Haemostasis*, 58, 1987, Abstract.

Tarnay, et al., "Pneumatic Calf Compression, Fibrinolysis, and the Prevention of Deep Venous Thrombosis", *Surgery*, Oct. 1980, pp. 489-496.

Templeton, et al., "Influence of Acute Myocardial Depression on Left Ventricular Stiffness and Its Elastic and Viscous Components", *The Journal of Clinical Investigation*, vol. 56, Aug. 1975, pp. 278-285.

Tiffany, et al., "Bolus Thrombolytic Infusions During CPR for Patients with Refractory Arrest Rhythms: Outcome of a Case Series", *Annals of Emergency Medicine*, 31:1, Jan. 1998, pp. 124-126.

Wobser, et al., "Intragastral Disintegration of Blood Coagula by Mechanical Vibration", *Endoscopy*, 10, 1978, pp. 15-19.

[No authors listed] Working Party on Thrombolysis in the Management of Limb Ischemia, "Thrombolysis in the Management of Lower Limb Peripheral Arterial Occlusion—A Consensus Document", *J. Vasc. Interv. Radiol.*, 2003, pp. S337-S349.

Yock, et al, "Catheter-Based Ultrasound Thrombolysis—Shake, Rattle and Reperfuse", *Circulation*, 1997, 95, pp. 1360-1362.

Zalter, et al., "Acoustic Transmission Characteristics of the Thorax", *J. Appl. Physiol.*, 1963, 18, pp. 428-436.

Ng, K. et al., "Therapeutic Ultrasound: Its Application in Drug Delivery", *Medicinal Research Reviews*, vol. 22, No. 2, pp. 204-223, 2002.

Tachibana, K. et al., "The Use of Ultrasound for Drug Delivery", *Echocardiography*, vol. 18, No. 4, pp. 323-328, May 2001.

Hull, W. et al., "Heat-Enhanced Transdermal Drug Delivery: A Survey Paper", *The Journal of Applied Research*, vol. 2, No. 1, Winter 2002.

Rapoport, N., International Cancer Research Portfolio Abstract,—award funding period Jan. 15, 1999-Dec. 31, 2002, Award code CA076562.

(56) References Cited

OTHER PUBLICATIONS

Cho, C-W, et al., "Ultrasound Induced Mild Hyperthermia as a Novel Approach to Increase Drug Uptake in Brain Microvessel Endothelial Cells", Pharm. Res. Aug. 2002, 19(8):1123-9.
Folts, D., "An In Vivo Model of Experimental Arterial Stenosis, Intimal Damage, and Periodic Thrombosis", Circ. 1991, 83 supp. IV:pp. IV-3 IV-14.
Folts, D., "Folts Cyclic Flow Animal Model", Contemporary Cardiology, Vascular Disease and Injury Preclinical Research, pp. 127-145, Humana Press Inc., Nov. 9, 2000.
Google Web Address: "Good Vibrations Personal Energiser—Vitafon—IR", Title: "Vitafon—IR for the temporary relief of pain". Google cache retrieval date, Apr. 29, 2006.
Kurtus, R: Google Address: "Hearing Pitch or Sound Frequencies—Succeed Through Using your Senses". Title: "Hearing Pitch Sound Frequencies", Mar. 7, 2001.
Google Web Address: "Frequency Hearing Ranges in Dogs and other Species", Title: "How well do dogs and other animals hear?", Google cache retrieval date Jun. 12, 2006.
Siegel R.J., "Ultrasound augmentation of thrombolysis and tissue perfusion", *Clin. Physiol. Funct. Imaging*, 2004, 24, pp. 156-163.
Coleman et al., "Therapeutic Ultrasound in the Production of Ocular Lesions", *American Journal of Ophthal.*, vol. 86, No. 2, 1978, pp. 185-192.
Coleman et al., "Application of therapeutic Ultrasound in Ophthalmology", *Progress in Medical Ultrasound*, 1981, pp. 263-270.
Christen, et al., "Effects of Intermittent Pneumatic Compression on Venous Haemodynamics and Fibrinolytic Activity", *Blood Coagulation and Fibrinolysis*, vol. 8, 1997, pp. 185-190.
Jackson, et al., "Antithrombotic Therapy in Peripheral Arterial Occlusive Disease", *American College of Chest Physicians*, 2001, 119: pp. 283S-299S, http://www.chestjournal.org/cgi/content/full/119/1_suppl/283S.
Lindblad, et al., "Effect of Vibration on a Canine Cutaneous Artery", *Am. J. Physiol.*, 250 (Heart Circ. Physiol. 19) pp. H519-H523, 1986.
U.S. Appl. No. 60/601,651, filed Sep. 27, 2007, Ward et al.
Antic S. et al, Music as an Auditory Stimulus in Stroke Patients, Coll Antropol., vol. 32, Feb. 2008 Suppl 1: pp. 19-23.
Chiu, W et al, Prolonged Stimulation with Sound Increases Angiogenesis . . . Abstract 1361—Feb. 24, 2004 Pub online http://www.aro.org/archives/2004/2004_1361.html.
Koiwa Y, Precordial or Epicardial Input of Phase—Controlled minute vibration: effect coronary flow rate in regional ischemia, New Horiz Fail. Heart Syndrome, 1996;117-130.
Massage Chairs.Co.UK—Advertisement on Internet http://www.massage-chairs.co.uk/understanding.massage.chairs.htm.

\* cited by examiner

PERCUSSION ASSISTED ANGIOGENESIS

1. COPENDING APPLICATIONS

This application is a continuation in part of application Ser. No. 11/036,386 entitled, "Hand Held Treatment Imaging Probe for Treatment of States of Low Blood Perfusion, filed Jan. 18, 2005 now abandoned, which is a continuation in part of application Ser. No. 10/902,122 entitled, Low Frequency Vibration Assisted Blood Perfusion Emergency System, filed Jul. 30, 2004 now U.S. Pat. No. 7,517,328, which claims the benefit of priority document CA 2439667 filed Sep. 4, 2003, entitled "Low Frequency Vibration Assisted Blood Perfusion System and Apparatus", the contents of which are expressly incorporated herein by reference.

2. FIELD OF THE INVENTION

This invention relates to a system for applying non-invasive, localized mechanical percussion to a human or animal body, to enhance expression and liberation of endogenous angiogenic mediators such as to induce or promote angiogenesis.

3. BACKGROUND

Vascular disease ultimately comprises the dominant killer and source of disability of men and women in the developed world.

Management of patients with advanced Coronary Artery Disease (CAD) in particular is a major challenge for the cardiologist and cardiac surgeon. Patients with advanced CAD frequently have limited symptoms with recurrent angina, angina at low work thresholds, breathlessness, and other debilitating conditions. These patients have often been through several "re-do" coronary bypass procedures and multiple percutaneous coronary interventions. Surgical and interventional options for these patients typically have been exhausted or will result in only partial revascularization. Therefore, therapy remains limited to the use of multiple anti-anginal medications, reduced activity, exertion, and stress level, and significant alteration and limitation of lifestyle.

The burgeoning field of therapeutic angiogenesis offers hope for these patients. The goal of this emerging approach is to therapeutically induce the growth and development of new vasculature in zones of severe ischemia in the myocardium, with the hope that new capillaries and arterioles generated will connect to remnant existing vasculature. These neo-vessels are viewed to act as collaterals, perfusing ischemic territories unapproachable by macro procedures such as angioplasty and bypass surgery.

Angiogenesis is a natural phenomenon, as narrowed arteries resulting in ischemia are known to promote (in some patients, to varying degrees) new arterial growth as an adaptive response—such that new arterial growth (including the development of pre-existing collateral vessels) is developed to circumvent the narrowings. The presence of such new arterial growth can limit symptomlogy and the size of a heart attack, or similarly in cases of cerebral ischemia, limit the infarct size and degree of damage caused by a stroke.

Several strategies are being pursued for therapeutic angiogenesis. Local injection of naked DNA or viral vectors coding for various angiogenic growth factors (eg, Vascular Endothelial-Derived Growth Factor (VEGF) and Fibroblast-derived Growth Factor (FGF) have been examined in animals and humans, as have local injections of actual growth factor proteins such as VEGF, FGF, and IGF. In addition, local delivery of endothelial cells and bone marrow-derived precursor stem cells are being studied. The corporation CARDIUM is currently evaluating an intra-coronary delivered pharmaceutical (Generx) for stimulation of coronary angiogenesis.

Intra-arterial injections of growth factors and other angiogeneic agents require an invasive catheterization procedure, which require a skilled operator with substantial infrastructure, and caries great cost to health care and substantial risks for the patient.

Another strategy that has recently been getting some attention is mechanically induced angiogenesis, as it has been scientifically shown in vitro and in-vivo that mechanical sheer stresses caused by hemodynamic forces, leads to endothelial liberation of beneficial mediators such as eNOS, VEGF and PCNA, and a large host of other beneficial mediators all known for stimulating angiogenesis.

In keeping with the above principles, non-invasive acoustic and mechanical delivery systems to the human body have been forwarded to assist angiogenesis, and in particular coronary angiogenesis.

Horzewski et al in U.S. Pat. No. 7,229,423 describes a piezoelectric actuator operable in the audible frequency ranges which delivers acoustic energy to the chest wall of a patient to cause increased uptake of angiogenic agents. The device offers very low micro-amplitude oscillations (considerably less than 0.1 mm) which cannot be felt by the patient, hence offering a limited therapeutic response to the target vessels. Similarly, many other piezoelectric actuators, mostly operable in the higher frequency ultrasonic ranges, have been proposed for use in causing angiogenesis, all of which provide limited penetrability to a targeted vasculature.

Kamm et al in US patent application 2003/00009119 A1 describes the use of external counter-pulsation techniques applied to the limbs or lower abdomen of a patient, to cause angiogenesis in the heart. The remote counter pulsation and use of periodic, gradual inflation and deflation of a pressure cuff, which increases the diastolic coronary blood flow velocity (and thus enhances coronary endothelial shear stresses) again offers a very limited, and almost insignificant agitative force/sheer forces which actually reach the coronaries.

Sackner in US patent application 20020103454 discloses a whole body "reciprocating movement platform" or bed which oscillates in a rhythmic to and fro motion (i.e. in the head to foot direction), delivering "external pulses" to a human body in the frequency range of 0.25-6 Hz, for a plurality of applications including stimulating angiogenesis. The 454 patent application invokes hemodynamic forces or "pulses" by virtue of the accelerations and deceleration's of the movement platform which purportedly instill sheer stresses from blood to endothelium of the vasculature; which is known to invoke the liberation of endogenous "beneficial mediators" such as t-PA, EDRF, and Nitric Oxide (all of which are of assistance in the improvement of blood flow and prophylaxis to disease). Again, the amount of forces which actually reach the target vasculature (such as the coronary arteries) are minimal as the oscillations are not of high intensity (i.e. they are at too low a frequency and are of too low and amplitude) and are not focussed upon the ischemic region.

As can be seen from the above, the prior art does not recite an acoustical method for inducing or assisting angiogenesis which reaches its vascular target with a high degree of efficiency.

A practical, low risk, non-invasive system to promote angiogenesis, and more particularly coronary angiogenesis via the use of high intensity mechanical reciprocating percussive force applied directly over, or proximate the ischemic region, such as to reach its target with highest efficiency is herein described.

4. SUMMARY OF THE INVENTION

A new non-invasive angiogenesis therapy system is disclosed, whereby an operator applies a series of low frequency percussions (or percussive massage) locally overtop (or overlying) a diseased vasculature of an ischemic region (such as preferably a vital internal organ), whereby the percussion waves directly penetrate to the ischemic region, cause sheer stresses and agitative forces to the endothelium of the arteries and arterioles which supply the ischemic region, and thereby cause new arterial blood vessel growth by virtue of the endogenous liberation of beneficial angiogenic mediators.

The present invention is based on the intuition that sustained non-invasive low frequency percussion (or impact vibration or oscillation by other comparable name) at a significant displacement amplitude (such that can be palpated by the patient) applied locally over an ischemic zone, yields particularly effective penetration and transmission to the blood vessels of the ischemic region, even those aspects of which (such as to vital internal organs including the heart and brain) may be acoustically shielded by attenuating structures, such as the chest wall, lung, or cranium.

Reversible ischemic regions, no longer approachable or treatable by existing invasive methods may be treated with this novel approach. The proposed therapy is preferably performed safely and non-invasively in a medical clinic, but may also be practiced at home by patient self administration.

The system provided is primarily adapted to serve patients with severe CAD (or other ischemic vital organs) in whom methods of revascularization such as angioplasty or coronary artery bypass surgery have failed or are not an option. The system may also be used however, to assist angiogenesis for other forms of vascular disease such as in the brain or periphery.

The percussion is applied via a series of consecutive, repeating, reciprocating impacts (or oscillations) at a frequency in the range of 1-1000 Hz (i.e. 1-1000 cycles per second, or in other words 1-1000 impacts over a period of one second), preferably at a frequency in the range of 1-200 Hz, and most preferably at a dual frequency of 8-15 Hz modulated by a higher sonic frequency of at least 20 Hz (or 20 impacts per second), and preferably in the 20-200 Hz range, such as to ensure adequate intensity to the vibratory waveform and to generally match the resonance frequency of target organs such as the heart and epimyocardium respectively, in order to yield a maximum internal agitative effect. The displacement amplitude of the applied percussion is in the range of 0.1 mm-15 mm, and preferably greater than or equal to at least 1 mm and most preferably greater than or equal to 2 mm (particularly in transthoracic coronary applications) to ensure adequate percussion agitative transmission to the targeted vascular region to achieve optimized angiogenenic therapy.

It is accordingly a general object of this present invention to define a utility for externally placed, low frequency percussion localized overlying the thoracic cavity (or generally upper torso) of a patient, as a cardiological treatment application which induces and assists coronary angiogenesis.

It is a further object of the present invention to provide an angiogenic percussion system which is adaptable to provide externally imparted low frequency vibropercussion to a variety of body regions suffering from chronic low blood perfusion, such as the body regions of the brain and the periphery.

It is a further object of the present invention to provide a preferred angiogenic percussion device which is of a size and shape to enable hand held engagement and operation, such as to add portability, maneuverability, and ease of placement of the vibrator to varying body surfaces, as well as a moduable or controllable means of applying engagement force by the hand or hands of an operator.

It is a further object of the present invention to provide a preferred angiogenic percussion device of the aforementioned type which enables a selectable maximum displacement amplitude control, such as to accommodate a tolerance level of a patient receiving angiogenic percussion therapy.

It is a further object of the present invention to provide a preferred angiogenic percussion device of the aforementioned type which operates to deliver a series of consecutive percussions applied within a frequency range of 1-1000 Hz, preferably within the range of 1-200 Hz and most preferably which enables emissions of a dual frequency underlying vibratory waveform in the 8-15 Hz range amplitude modulated on a higher frequency "carrier wave" in the range of about 20-200 Hz (i.e. 20-200 impacts per second), such as to match the resonance frequency of key internal organs such as the heart and epimyocardium within the thoracic cavity for optimized coronary angiogenic effect.

It is a further object of the present invention to provide a preferred angiogenic percussion device of the aforementioned type with a selection of percussive/body surface attachment interfaces, such as to accommodate a preferred method and/or skill level of an operator in order to enhance angiogenic percussion transmission and effectiveness.

It is a further object of the present invention to provide a percussive/body surface attachment interface of the above type, comprising at least one contact (or contact node) adapted in size and shape to enable efficient seating within a rib space of a patient in order to optimize angiogenic percussion transmission to the chest wall and vascular structures within the thoracic cavity.

It is a further object of the present invention to provide a percussive/body surface attachment interface of the above type, comprising a pair of preferably adjustably spaced contacts (or contact nodes) such as to enable contact to a pair of application sites preferably bridging the sternum (or bridging any other bony structure upon the thoracic cavity such as the spine or ribs) of the patient, in order to improve penetration to the mediasteinal cavity, and preferably match the anatomic configuration of the base of the heart wherein the coronary anatomy is substantially distributed.

It is a further object of the present invention to provide a percussive/body surface attachment interface of the above type, comprising a plurality greater than a pair of contacts (or contact nodes), such as to enable contact at a plurality of application sites (or intercostal space levels) preferably bridging the sternum of the patient, in order to maximize penetration to the heart which is variably situated depending on the anatomy of the patient.

It is a further object of the present invention to provide a preferred percussive/body surface attachment interface of the above type comprising an ultrasonic imaging transducer, and most preferably a phased array ultrasonic imaging transducer, either alone, or preferably situated on an anatomically leftward oriented contact (when a plurality of contacts are used), such as to enable real time ultrasonographic imaging and/or Doppler readouts such that a skilled operator (when available) may optimize penetration and target angiogenic percussion to a culprit vascular region or target area while concurrently imaging or interrogating the target.

It is a further object of the present invention to provide a percussive/body surface attachment interface of the above type, which in addition to supplying the means of transmitting low frequency angiogenic percussion from a oscillation source to a patient, is additionally enabled to emit a therapeutic low frequency ultrasonic wave form such as to provide a pair of therapeutic oscillating wave forms (i.e. low frequency vibration plus low frequency ultrasound, or more broadly oscillations in about the 1 KHz-500 kHz range) in concert.

It is a further object of the present invention to provide percussive/body surface attachment interface of the above type, which is not only enabled to transmit low frequency angiogenic percussion from an oscillation source and concurrently emit a low frequency ultrasonic treatment wave form (or more broadly oscillations in the 1 KHz-500 KHz range), but is additionally enabled to provide ultrasonographic imaging (e.g. real time 2D, 3D and/or Doppler) such that an operator may optimize penetration and target low frequency angiogenic percussion and low frequency emissions in the 1 KHz—to about 500 KHz range to a culprit vascular region or target area while concurrently imaging or interrogating the target.

It is a further object of the present invention to provide an angiogenic percussion method and apparatus for enabling cardiac phase controlled percussion delivery. Cardiac phase controlled angiogenic percussion is of particular importance in cases of known LV dysfunction as percussion limited predominantly to the diastolic cardiac phase provides a positive inotropic effect, in addition to mechanical agitation and sheer forces of the epimyocardium of the heart and coronary arteries thereupon which cause angiogenesis.

It is a further object of the present invention to provide an angiogenic percussion device of the aforementioned type which enables random changes to at least one percussive or vibratory waveform characteristic such as; displacement amplitude, force, frequency, duty factor, directivity, wave shape, and vibratory pattern, such as to improve the efficiency of percussion in providing liberation of endothelial derived angiogenic mediators, and additionally serve as an alternative means for treatment of blood flow disturbances in general.

It is a further object of the present invention to provide an alternative, low tech angiogenic percussion system which is simple and easy to use, without a skill requirement beyond what a nurse, paramedic, or even the patient (i.e. by self administration) could typically provide, such as at home or in an office setting.

5. BRIEF DESCRIPTION OF THE DRAWINGS

The apparatus and method of the present invention will now be described with reference to the accompanying drawing figures, in which.

6. DETAILED DESCRIPTION AND PREFERRED EMBODIMENT

Figure 1:
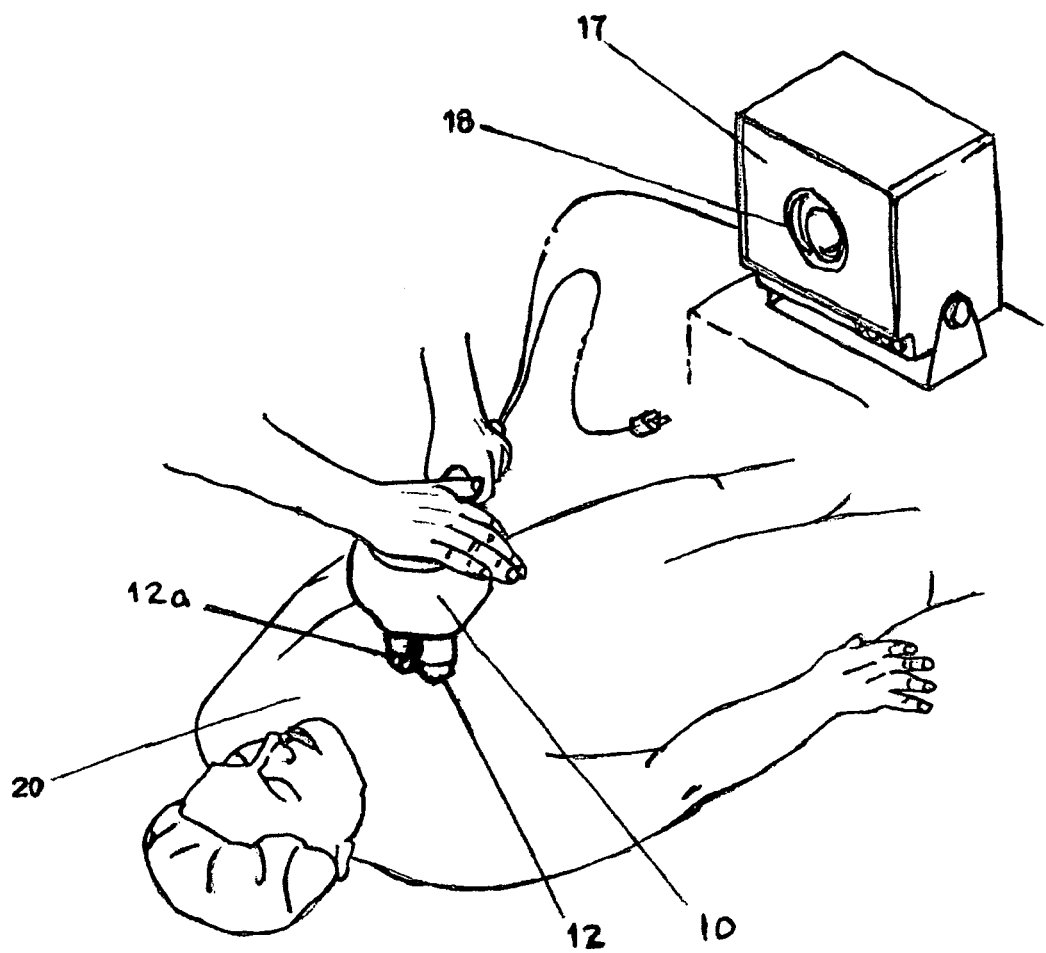
FIG. 1 is a perspective view of a preferred angiogenic percussion device for use in a medical clinic with a pair of contacts spaced to bridge the sternum of a patient, with the anatomically leftward contact containing an ultrasonic imaging transducer, thereby enabling ultrasonic imaging targeted vibration by a hand held technique according to the invention.

The present invention generally provides a method of treating vascular disease by inducing angiogenesis. A patient suffering from vascular disease (preferably arterial disease) is provided, and a percussion device (herein after "angiogenic percussion device") which can provide external percussion localized over the diseased arterial vaculature supplying the target ischemic region is attached to the patient's external body surface generally overlying or proximate the diseased vasculature. The apparatus is used to repetitiously impact vibrate (or repeatedly percuss against) the external body surface at a sufficient intensity (i.e. generally a palpable amplitude) to enable effective penetration such as to induce angiogenesis. Without wishing to be bound by a particular theory, the external percussion is thought to induce angiogenesis by altering the shear stress or other mechanical force experienced by the cells of the patient's coronary vasculature. This change in shear stress leads to the production of various angiogenic factors by the endothelial cells, and these factors subsequently act on various cells to induce the growth of new blood vessels.

It is preferred to establish optimal transmission to the heart. Angiogenic percussion therapy is thereby provided in conjunction with high frequency diagnostic ultrasonography (i.e. "HFUS" around 1-50 MHz, preferably 1-5 MHz, most preferably to achieve optimized transthoracic penetration, 1-2.5 MHz) in order to target angiogenic percussion in coronary applications. In this preferred "imaging" embodiment, a "dual function", simultaneous angiogenic percussion and imaging system is employed via a single combined imaging/treatment probe. In this preferred embodiment, low frequency angiogenic percussion therapy is advantageously employed in conjunction with high frequency ultrasonography (i.e. HFUS), where both high and low frequency wave forms are applied simultaneously (i.e. in real time) via a single hand held instrument, which comprises an ultrasonic imaging transducer operatively connected (or acoustically coupled) to the active end of a low frequency angiogenic percussion source (preferably a linear stepper motor, described in detail later) operational to emit oscillations (or reciprocating motion) in the 1-1000 Hz (or 1-1000 Hz impacts/second) range. The ultrasound imaging transducer in this case acts as a percussive attachment interface (or contact) to the patient 20, thereby enabling the transmission of low frequency angiogenic percussion from the angiogenic reciprocating percussion source, while concurrently enabling real time ultrasonic imaging, which may comprise 2D or 3D real time imaging) to direct angiogenic percussion.

The method of this preferred dual function system comprises the placement of the imaging/treatment probe (with the accompaniment of ultrasonic conduction gel) to the skin of the patient 20 by a trained clinician or technologist in a medical clinic, such as to establish a sonic penetration window depicting a target of low frequency angiogenic percussion. Once a sonic penetration window is established, a series of low frequency angiogenic percussions are initiated and transmitted through the ultrasound imaging transducer attachment interface, and the application site is additionally maintained through continued monitoring of the ultrasonic image provided. In this manner, intelligible anatomic placement and to a degree angulation of the imaging treatment probe is achieved and maintained, thereby optimizing the delivery of low frequency angiogenic percussion therapy to the culprit vascular region targeted.

Referring to FIG. 1, a patient 20 undergoing percussion therapy according to the preferred dual function embodiment in a coronary angiogenesis application is shown (intravenous line, oxygen prongs, and monitoring equipment preferably applied for applications in a medical clinic—not shown). The preferred engagement means, the hands of an operator, for applying low-frequency percussion via an angiogenic percussion device 10 to the patient 20 via a pair of contacts 12 and 12a, spaced to enable seating to the rib spaces to either side of the sternum is shown. The anatomically leftward oriented contact (hereinafter percussive ultrasonic imaging contact 12a) advantageously comprises an ultrasonic imaging transducer, and most preferably a phased array ultrasonic imaging transducer (which is best suited to cardiac applications, discussed later), such as to enable targeting of percussion via a real time multidimensional image 18 (in this case a 2D image) on a ultrasonic display 17.

The contacts 12 and 12a of angiogenic percussion device 10 are placed at the treatment site upon the chest wall of the patient 20, and an acoustic window yielding an image of the septal and posterior-lateral wall of the heart is preferably established and a series of percussions at high displacement amplitude (preferably with the highest peak displacement amplitude setting tolerable and judged safe to patient 20) are established. Percussion applied across the sternum is preferred, as the oscillating sternum in tandem with contacts 12 and 12a assist in transmission of chest wall percussion to the heart lying directly underneath.

In coronary cases treated in a medical clinic, the recommended application time is 20 minutes to half an hour, 3 to 5 times per week. An intravenous line is established for introduction of medications in case of complications. Sedatives and anti-nausea medication should be made ready in a drug tray. ECG, O2 saturations and blood pressure should be monitored by a trained attendant. A superficial administration of lidocaine to the skin of the chest wall application site may be considered in select patients. Oxygen should be administered if necessary to assist breathing.

For use of angiogenic percussion device 10 in cardiac applications, the patient 20 is preferably placed supine, although two pillows behind the head may be allowable if the patient 20 tends to experience shortness of breath. Next, the contacts 12 and 12 a of the angiogenic percussion device 10 are placed against the target sites, preferably bridging the sternum upon the chest wall of the patient 20. The spacing between contact 12 and 12a are manually adjusted by a control upon angiogenic percussion device 10 (not shown), and contact 12a is manually rotated on its axis via another control (also not shown), such as to enable the procurement of standardized echocardiographic views while an operator holds the angiogenic percussion device 10 otherwise static. Once a desired echocardiographic window and image is obtained, such as to show acoustic penetration preferably to the septal and posterior lateral wall of the heart, angiogenic percussion device 10 is turned on, (preferably initially at a low peak displacement amplitude level such as 0.1 to 1 mm), where after the displacement amplitude and engagement force is gradually titrated upwards to a point of tolerance for the patient 20.

In an alternative method, which may be used with or without echocardiographic guidance, a plurality of greater than a pair of contacts 12 (or 12a) may be employed, such as to enable seating to a plurality of rib spaces at differing intercostal space levels upon the chest wall of patient 20, such as to increase tissue coverage and thereby improving the likelihood of penetration to the target ischemic myocardium of the heart which is variably situated within the thoracic cavity depending on the anatomy of the patient. Co-pending U.S. patent application Ser. No. 10/902,122 to Hoffmann discloses exemplary attachment interfaces suitable to transthoracic applications and, and is incorporated herein to the present invention by reference.

Figure 2:
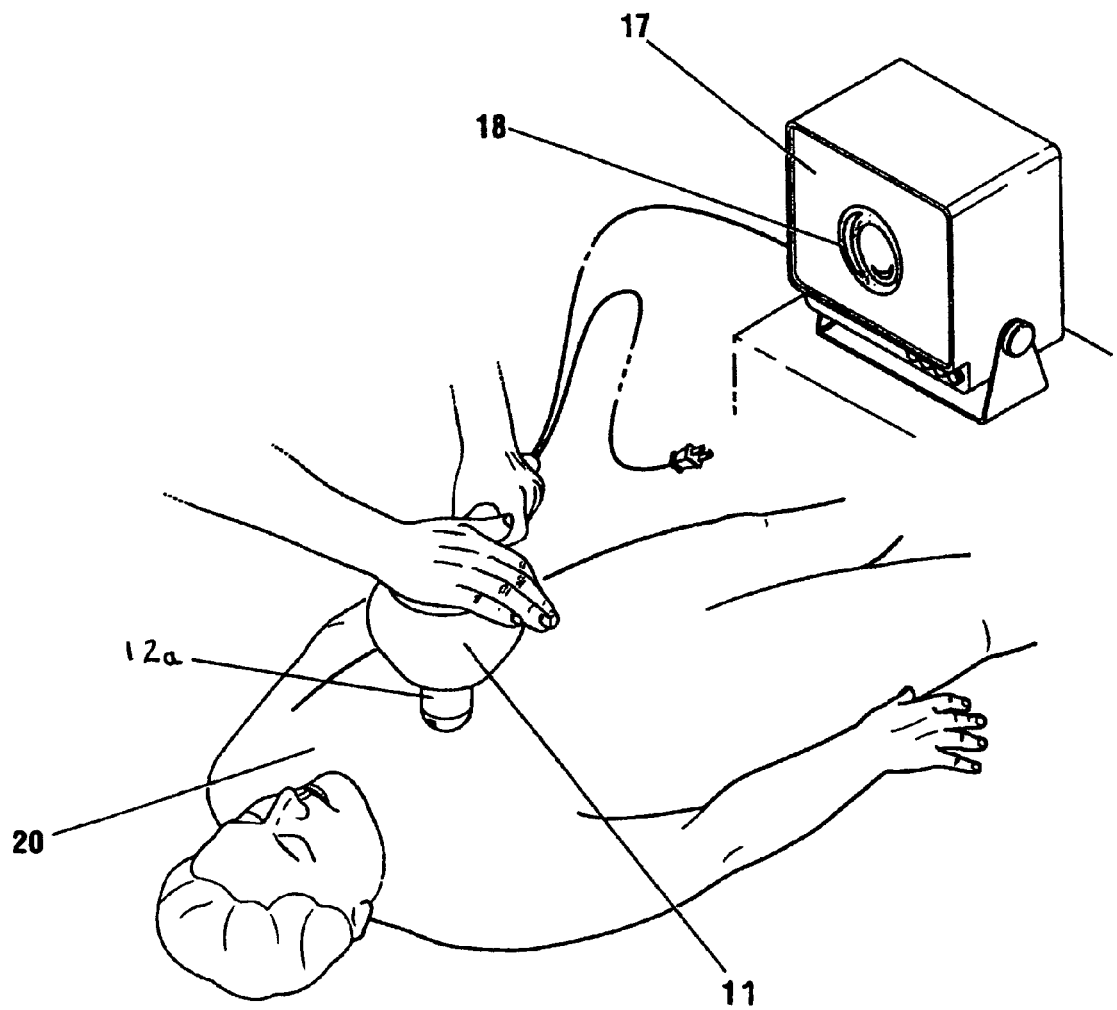
FIG. 2 is a perspective view of a variant angiogenic percussion device incorporating a single contact comprising an ultrasonographic imaging transducer, such as to enable superior angulation potential of the device via a hand held technique according to the invention.

In reference to FIG. 2, a variation to the preferred angiogenic percussion device 10 (angiogenic percussion device 11) is depicted wherein a solitary contact comprising a solitary percussive ultrasonic imaging contact 12a is utilized. This variation allows superior angulation of the percussive ultrasonic imaging contact 12a within an acoustic window and thereby superior "pointing" of the percussive forces towards a selected ischemic myocardial region. This variation may be particularly valuable for patients with difficult acoustic windows, such as in chronic obstructive lung disease (COPD) where the lung (air) substantially covers the heart, and limits vibratory transmission making imaging and establishment of a satisfactory acoustic penetration window particularly difficult.

In a further variation aimed to optimize angiogenic therapy, low frequency ultrasonic treatment (LFUS) may also be utilized in combination with HFUS imaging and low frequency angiogenic percussion in the 1-1000 Hz range, via a variant "multifunction system" employing a single variant LFUS enabled imaging/treatment probe (not shown). In this variation to the preferred embodiment, low frequency angiogenic percussion therapy is employed in conjunction with high frequency ultrasonography (i.e. HFUS) and "treatment" low frequency ultrasound (i.e. LFUS) simultaneously and in real time, where all three wave forms are applied in concert via a single transmission instrument. In this manner, direct HFUS imaging and targeting may be combined with low frequency angiogenic percussion in the 1-1000 Hz range, and low frequency ultrasonic energy (at around 1 KHz-500 KHz, preferably 20-100 kHz, most preferably about 27 kHz), to optimally apply mechanical oscillatory forces to the culprit vascular region targeted.

Duty factor and intensity level may be selected with respect to the LFUS application (i.e. in the multifunction system), such as to provide the means to avoid undue heating to the skin surface of the patient 20. Alternatively, a wet cool cloth applied intermittently to the skin surface, and/or a periodic change of application site (or even transmission instrument), may be utilized to prevent skin burning of the patient 20 during joint LFUS use.

The use of a combined imaging/treatment probe, (or "single transmission instrument"), regardless of employment of the preferred "dual function" or variant "multifunction" system, at least initially involves a skilled imaging technique to direct angiogenic percussion therapy to the ideal sonic penetration window. The use of both hands to support and maintain the imaging/treatment probe with enough engagement force to the chest wall is suggested, or the operator can alternatively, use one hand, or utilize a clamp or belt (neither shown), as long as the appropriate sonic penetration window is visually monitored and maintained. An inertial weight may be placed to the backside (or optionally within housing) of the chosen "transmission instrument" particularly for cardiac applications, adding inertia to the apparatus and thereby assisting the operator ergonomically who may hold the transmission instrument in position by hand.

While the supine position for the patient is generally preferred in cardiac applications, different patient positioning (e.g. with the patient lying to some degree on his or her left side, up to the left lateral debecutis position) could be utilized as per the judgment of the operator, especially when trained in cardiac ultrasonic imaging, in order to establish the highest quality and most stable sonic penetration window available. The parasternal windows remain the preferred application site if available (i.e. in coronary applications), however other sonographic windows may be considered.

The next step in the preferred treatment method in coronary angiogenesis applications is to apply appropriate engagement force and determine maximum peak displacement amplitude to the chest wall of the patient 20 with angiogenic percussion device 10. The attending clinician applies force to angiogenic percussion device 10 against the target area by hand, or alternatively via differing engagement selections of a clamp, or other fixture such as by belt or vest (neither shown). A relatively constant, firm engagement force of at least 5-10 N, preferably 20-100 N, and optimally 50-100 N, should be obtained according to the tolerance and safety of the patient 20. The engagement force should preferably not exceed 100 N, such as to avoid possible dampening of oscillations of the angiogenic percussion device 10 or injury to the patient 20. A force meter (not shown) may be optionally utilized to confirm engagement force. In the preferred case where the angiogenic percussion device 10 is engaged by the hand or hands of an operator, the engagement force can be monitored, maintained and modulated as per the articulated needs (or tolerance levels) of the patient 20. Referring back to FIG. 1, the housing of the angiogenic percussion device 10 is advantageously "L" shaped, incorporating a handle to facilitate hand held operation. Engagement of the angiogenic percussion device 10 preferably precedes activation, however alternatively the angiogenic percussion device 10 may be engaged after activation of percussion to the patient 20, at the discretion of the operator. The chest wall is the preferred placement site of angiogenic percussion device 10 as the heart is generally situated in the anterior third of the thoracic cavity.

As a rule of thumb for coronary applications, the engagement force should include the maximum force, which is tolerable for the patient 20, and will not cause the angiogenic percussion device 10 to significantly dampen (or stop) its percussive oscillations. Satisfactory engagement is further identified once the patient 20 identifies a "fluttering" in the teeth or jaw (or exhibits an undulation in the voice) which indicates efficient transmission. It should be noted that patient comfort can be greatly improved by moving the application sites about, even slightly within the rib spaces, or alternatively to differing rib spaces (in keeping to the selection of methods previously described).

Angiogenic percussion therapy preferably continues with selection of the maximum peak displacement amplitude or force setting judged safe and tolerable to patient 20. This maximal setting, may result in mild bruising to the chest wall (or other body surface treated), and an informed consent should preferably be signed by the patient 20 if feasible. It should be understood that the exact order (or selection of steps) in the application of engagement force vs. peak displacement amplitude level of the angiogenic percussion device 10 against the body surface of the patient 20 is not critical, as long as the end result (i.e. for angiogenic percussion therapy) is that a firm engagement force (i.e. at least 5-10 N, and preferably within the range of 20-100 N) at a high maximal displacement amplitude (i.e. greater than about 1 mm preferably, and preferably in the range of at least 2-15 mm, and ideally maximized to patient 20 tolerance) is ultimately established.

If maximal displacement amplitudes settings of less than or equal to about 2 mm, and/or engagement forces of less than approximately 20 N (i.e. approximately the weight of the device) are not tolerated to the chest wall of the patient 20, then patient 20 may optionally be placed in the prone position (not shown) and the contacts 12 and 12a may be placed to bridge the spine of patient 20 in the upper thoracic region. Angiogenic percussion at higher displacement amplitudes (often tolerable to about 6-15 mm), and higher engagement forces (often tolerable to 50-100 N or greater), may be safely an comfortably utilized in the majority of these cases, to ensure and maximize penetration to the mediasteinal cavity and enhance clinical effectiveness of angiogenic percussion. Alternatively, patient 20 may be placed upon a chair or stretcher wherein a suitable angiogenic percussion source is disposed upon or within the upholstery of the chosen furniture item, such as to enable angiogenic percussion delivery to the upper back of patient 20. Percussion across the spine of a patient (at roughly the fifth intercostal space level) is particularly effective alternative to chest wall percussion for cases of known posterior, or infero-posterior ischemia, as percussion across the spine transmits vibration forces via the spinal process to the aorta, which thereafter with reasonable efficiency transmits vibratory forces to the posterior wall of the heart.

Tests by the applicant have shown that low frequency percussive penetration through soft tissue is generally related to the applied displacement amplitude and engagement force of the vibratory contact to the body surface vibrated. It has been ascertained that the desired engagement force of an angiogenic percussion source placed against the chest wall of the patient 20 is preferably at least 5-10 N, and optimally at least 20 N, and up to 100 N (when tolerated), to confer ideal penetration. When percussion is applied to the muscle groups adjacent to the spine of the patient 20 (as an alternative means of transthoracic angiogenic percussion to the mediasteinal cavity), engagement force can be much higher (i.e. greater than 50-100 N may be utilized), as the application is far better tolerated by the patient 20, and higher engagement force and displacement amplitudes are generally required to achieve therapeutic levels of mediasteinal cavity penetration.

Optimal displacement amplitudes also vary significantly with the constitution and tolerance levels of the patient 20, as well as the selected body surface treated. Angiogenic percussion displacement amplitudes of at least 1 mm (and preferably in the range of at least about 2 mm-6 mm), are preferred for chest wall applications, and displacement amplitudes of at least about 4 mm-mm are preferred for transthoracic applications from the backside of the patient 20. In the case where ultrasonic (HFUS) imaging is employed to direct or target angiogenic percussion therapy, penetration to the heart is generally increased, and higher amplitudes and engagement forces of angiogenic percussion (i.e. which may cause bruising to the skin surface vibrated and patient discomfort) are not absolutely required. Still however (regardless of the use of HFUS enabled directed therapy), the highest possible combination of engagement force and peak displacement amplitude is still recommended to yield best results in treatment of coronary disease. Once placement site, peak amplitude and engagement force of angiogenic percussion device 10 is established, the operator will select a form of angiogenic percussion therapy, where frequency, and percussive waveform and/or percussive pattern is defined.

In the case that the patient 20 is unable to tolerate even modest levels of angiogenic percussion (i.e. both displacement amplitude and engagement force, regardless of body surface vibrated), then a gentle application utilizing the weight of the angiogenic percussion device 10 (or at the least 5 newtons of engagement force via use of for example a smaller, lighter weight device) and the maximum peak low level of displacement amplitude tolerable to patient 20 should be utilized. Peak displacement amplitudes of 1-2 mm (or even less, e.g. 0.1-1.0 mm may be utilized) in these cases.

In general, in the preferred embodiment of the present invention the percussion delivered is comparable to the resonant frequencies of the targeted internal organs (such as in the range from 1 Hz-50 Hz for most internal organs, and preferably in the range of about 8-15 Hz in cardiac applications) intermixed or modulated with a higher frequency "carrier wave" which matches the resonance frequency of the tissue within the internal organ, which often houses or is attached to the diseased vasculature in need of angiogenesis (such as around 20-200 Hz, and most preferably 20-120 Hz for cardiac applications). The result of multiplying one frequency by another (Amplitude Modulation [AM]) is the carrier plus or minus the modulators. The present invention takes advantage of the fact that the human body is a nonlinear medium in which modulated frequencies are demodulated. Thus, in order to attain for example an 8 Hz and an 80 Hz frequency (which approximates the resonance frequency of the heart and epimyocardium respectively) within the targeted tissue, a modulated combination of, a 80 Hz (or 80 impacts per second) carrier wave modulated by an underlying 8 Hz input may be administered. Outside the body, the result would be the carrier (80 Hz+/−8 Hz). However within the body (a nonlinear medium), the signal is demodulated to the independent components of the vibratory percussive waveform. As a result, the targeted tissue receives vibratory energy at a frequency of 8 Hz and 80 Hz via a parametric demodulation. Additional combinations of carrier and modulator frequencies may also be used depending on the tissue targeted, and their differing acoustic resonance frequencies and geometries.

The angiogenic percussion is employed via a series of percussions delivered within a frequency range of 1-1000 cycle per second (or 1-1000 impacts per second) according to the present invention. As mentioned above, it is preferable to match the resonance frequency of the heart (as an entire organ) and also the epimyocardium within the heart, which generally falls generally within the 1-200 Hz range, and more specifically within the 8 Hz-15 Hz and 20-120 Hz range respectively such as to attain maximum agitative internal effect. Hence, the preferred angiogenic percussive waveform is preferably delivered at a lower frequency in the 8 Hz-15 Hz range (resonance frequency of the heart) which is amplitude modulated upon a higher frequency in the 20-200 Hz, and most preferably in the 20-120 Hz range (resonance frequency of the epimyocardium). The heart and epimyocardium, receiving angiogenic percussion stimulus at or near its resonance frequency will vibrate with the highest possible displacement amplitudes at the localized areas which best receive the signal. External angiogenic percussion at the resonance frequency enables transmission of the angiogenic percussion signal internally throughout the ventricular chambers with highest efficiency, thereby vibrating the entire heart and effecting optimal intra ventricular transmissibility. Optimal intra ventricular transmissibility aids agitation of the entire coronary tree, including those parts of the tree hidden behind lung or soft tissue which are poor transmitters of angiogenic percussion and therefore otherwise difficult to penetrate directly with sonic mechanical energy. It should be understood that while a dual frequency is preferred such as to match the resonance frequency of the both heart and epimyocardium in tandem, a singular frequency locally applied over the upper torso of at least 8 impacts/second (resonance frequency of the heart) would supply a minimal adequate level of mechanical energy to endothelial sheer stresses to invoke coronary angiogenesis.

Higher frequencies (i.e. 200-1000 Hz), or even in the sub-ultrasonic to ultrasonic range (i.e. 1000 Hz-500 kHz), while optional for causing angiogenisis, are generally higher than the resonance frequency of the heart and epimyocardium and hence not readily transmissible to all areas of the coronary anatomy by intra ventricular transverse transmission means. Higher frequency angiogenic percussion also requires diminished displacement amplitude for safe clinical use, which is a further limitation to this wave-form's potential penetrating and agitative power (i.e. through the chest wall or other body part treated). A directed approach through an identifiable sonic penetration window to ensure adequate penetration to target areas by the much weaker (i.e. lower displacement amplitude—in the low millimeter to sub millimeter ranges) signal is particularly recommended for frequencies greater than 200 Hz, again at the highest amplitudes and forces judged tolerable to a patient.

Generally, angiogenic percussion device 10 enables a range of frequencies selectively chosen between 1-1000 Hz, with a selection of multiple displacement wave-forms, displacement amplitudes, percussive waveform patterns (including non-randomized and randomized vibratory waveform and waveform patterns—described later), amplitude modulated frequency waveforms, and cardiac phase selected percussion emissions. The present invention provides such a broad range of waveform parameters, as the apparatus and system is optionally employed both as a treatment system and a research tool.

For treatment in the cardiac clinic, the patient 20 should preferably be monitored by at least one clinician or technologist during the course of angiogenic percussion therapy. An adjustment in the amplitude or engagement force of angiogenic percussion may be required depending on patient tolerance. The position of angiogenic percussion device 10 may also need to be periodically re-adjusted. The operator can readily adjust or remove the angiogenic percussion device 10 (or provided variant) as required.

Particularly the operator or clinician may adjust the treatment to suit the physiological status of the patient, such as in a sudden drop in blood pressure, which may indicate deterioration into heart failure. The operator may decide to discontinue "continuous" angiogenic percussion therapy (i.e. angiogenic percussion applied throughout the cardiac cycle), which in some cases may have a negative inotropic effect on left ventricular function, and switch to "diastolic" timed angiogenic percussion, which is known to provide a positive inotropic effect and is also known to improve coronary flow. If hemodynamic compromise is borderline, the operator may optionally limit or reduce the maximum displacement amplitude setting of angiogenic percussion selectively during the time period of ventricular systole, while maintaining a greater maximized displacement amplitude during ventricular diastole.

Furthermore, the operator may optionally select percussion emissions with at least one randomized waveform parameter (hereinafter "random percussion"), whereby the mutivectored convection currents and force vectors generated may in some circumstances lead to liberation of angiogenic mediators with a particularly high efficiency. Random changes to at least one percussion waveform characteristic such as; displacement amplitude, force, frequency, duty factor, directivity, wave shape, and vibratory pattern, are conceived according to the invention. If randomic vibration is utilized it is preferred to utilize a randomic percussion pattern generally in the 8-15 Hz range modulated by a 20-120 Hz signal such as to achieve optimum intra-ventricular resonance response in cardiac applications.

Figure 3:
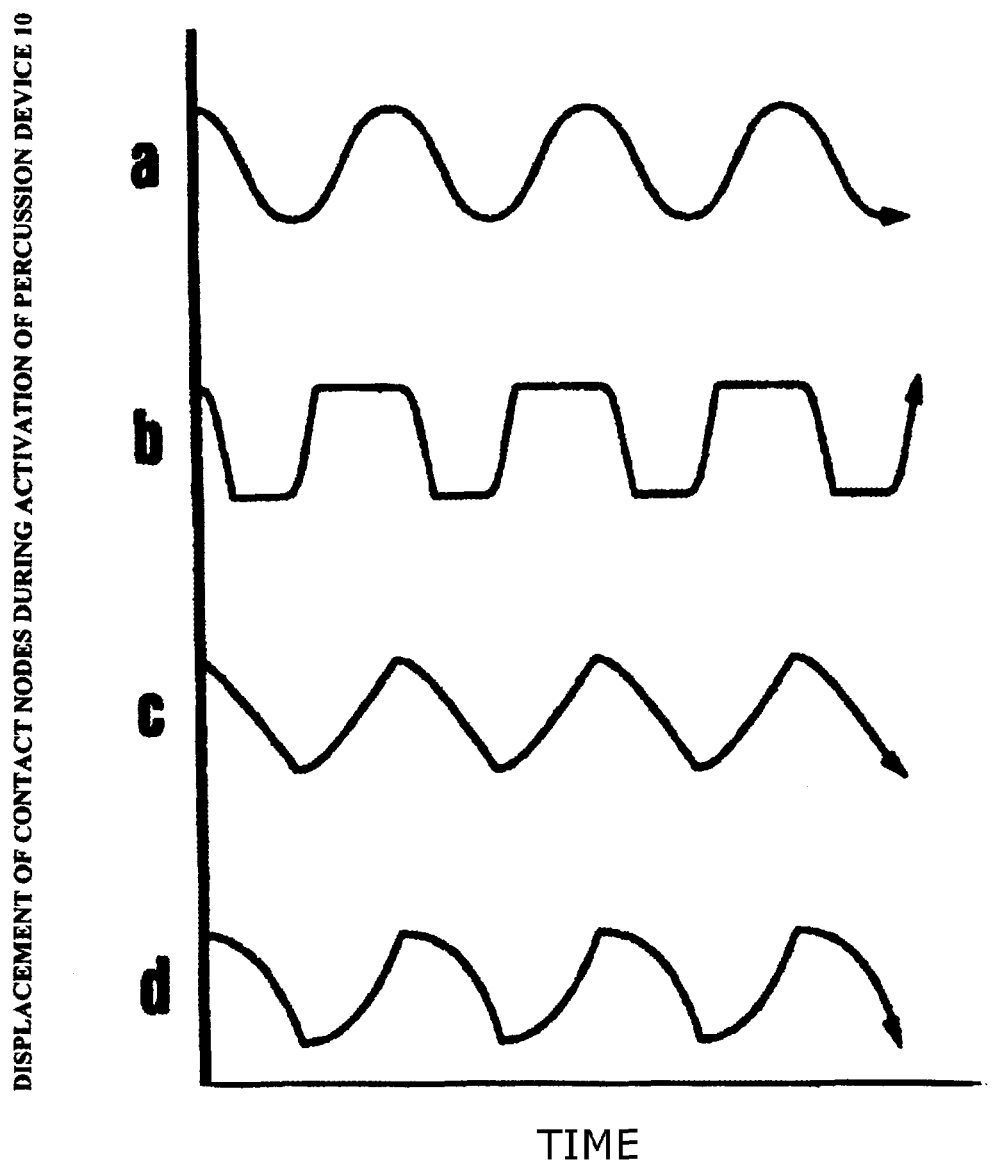
FIG. 3 is a graphic illustration of a variety of percussion displacement waveforms according to the invention.

In reference to FIG. 3, low frequency percussion via a plurality of displacement wave forms with "displacement" on the vertical axis and "time" on the horizontal axis, (with respect to the movement of contact 12 and 12a) is shown. The preferred embodiment incorporates use of a sinusoidal percussion displacement waveform <a>, which best accommodates modulation with a second sinusoidal signal, however other displacement wave forms of percussion may alternatively be selected such as; square waves <b> (or pulsed or percussive waves with a steep displacement rise by other name), saw tooth waves <c> (with a gradual displacement rise), exponential waves <d> (with an acceletory, non-linear displacement rise) or any other linear or nonlinear wave shape (or combinations thereof) according to the invention.

Figure 4:
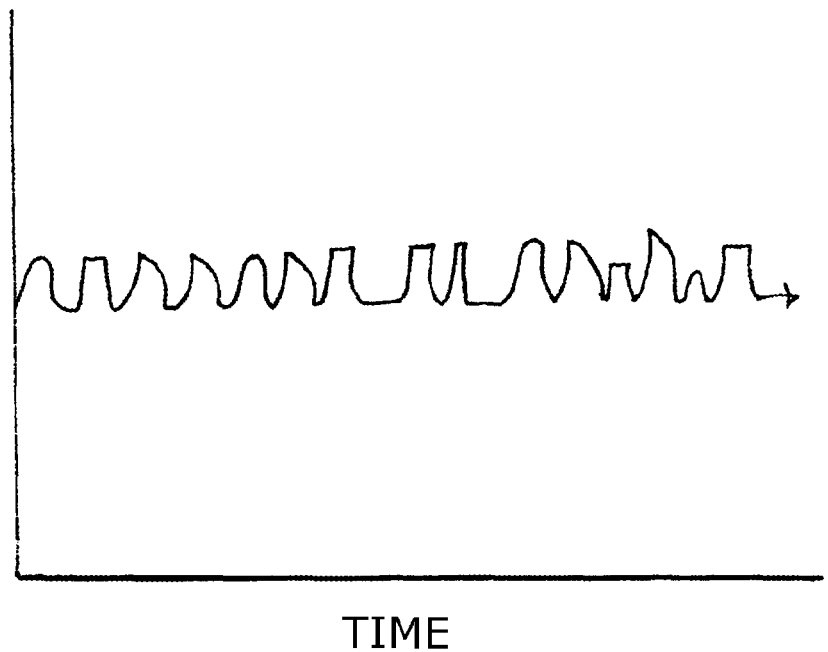
FIG. 4 is a graphic illustration of an example of a randomic angiogenic percussion waveform, according to the invention.

In reference to FIG. 4, low frequency randomic angiogenic percussion via a plurality of displacement wave forms with "displacement" on the vertical axis and "time" on the horizontal axis, (with respect to the movement of a contact 12 and 12a) is shown. By way of example only, sinusoidal, square, exponential (sawtooth) waveforms are randomly depicted, with varying cadences, and displacement amplitudes. Randomic vibration may in some circumstances enhance the endothelial liberation of angiogenic mediators because of the ensuing chaotic, multivectored convection currents which best mimic the natural phenomenon of hemodynamic sheer stresses (believed causative of angiogenesis) which result as high velocity blood flow crosses a narrowing in an artery, such as a coronary artery.

Randomly varying percussive wave shapes and frequency (e.g. randomly varying within the frequency range of 20-120 cycles/second, combined with a varying 8-15 cycle/sec modulator) at or near peak tolerable displacement amplitude is an optional approach for coronary, angiogenesis randomic percussion applications.

Figure 5:
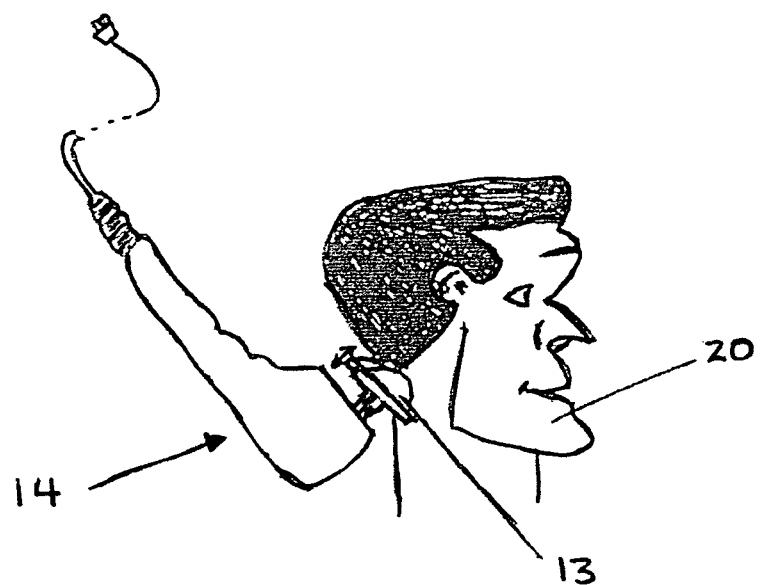
FIG. 5 is a perspective view of a patient receiving treatment from a variant angiogenic percussion device for causing cerebral vasculature angiogenesis according to the invention.

In reference to FIG. 5, a schematic representation of a variant angiogenic percussion device 14 applied to the base of the skull via a pair of contacts 13 (superior aspect of the posterior region of the neck) for cerebral angiogenesis applications is shown.

Treatment for cerebral vasculature ischemia, in contrast to transthoracic treatment of the coronary vasculature, is preferably quite gentle, with a maximum displacement amplitude setting (preferably applied to the posterior region of the neck adjacent and pointing towards the base of the skull) generally less than or equal to about 2 mm. Application of angiogenic percussion to the posterior neck is preferred because it is very comfortable and relaxing to the individual treated. It should be understood however that other attachment regions to the skull itself or differing parts of the neck may also be used alone or in tandem according to the invention. Treatment durations for cerebral angiogenesis applications are preferably short, such as about 15-20 minutes three to five times per week, however longer or shorter angiogenic vibration treatment sessions may be used as well.

Alternatively, angiogenic percussion (or vibration) may be applied directly to the cranium of the patient 20 (not shown), again at a relatively low maximum displacement amplitude to avoid bruising to the head of patient 20. A frequency of less than 1000 Hz, and preferably selected from the 1-200 Hz, and most preferably 8-25 Hz modulated upon a signal in about the 20-200 Hz range; is then applied with a peak, maximal selected displacement amplitude (i.e. from 0.1 mm to 15 mm, however preferably less than or equal to about 2 mm displacements, and most preferably less than or equal to about 1 mm displacements). A pair of head phones with music played may also be used—which is a variant form or angiogenic percussion therapy according to the invention, wherein the physical contact of the head phones to the earlobes and/or cranium of the patient transmits a gentle form of percussive vibration.

Referring again to FIG. 1, the preferred embodiment of the angiogenic percussion device 10 (i.e. in the chronic treatment of CAD) is applied by the hands of a skilled operator with the patient 20 lying substantially in the supine position.

Angiogenic percussion device 10 contains a linear stepper motor (not shown), with sufficient power to enable operation at engagement forces of up to approximately 100 N. Angiogenic percussion device 10 is characterized to enable selective frequency and displacement amplitude control, with modulated or singular frequency waveform patterns, in the 1-1000 Hz and 0.1-15 mm range respectively, as well as selectable displacement "wave form" control (comprising a selection of sinusoidal, square, saw tooth, and exponential wave shapes, or any other programmable variation of linear or nonlinear displacement wave shapes—or combination thereof. Use of angiogenic percussion device 10 enables a series of percussions at the selected percussive settings to the selected body surface treated. The angiogenic percussion device 10 preferably offers selectable cardiac phase emission control, and a regular "non-randomic mode" with selectable non-randomic (fixed value or unwavering pattern) frequency, displacement amplitude, vibratory pattern, duty factor and selectable waveform control, and a "randomic mode" where any number of the above characteristics will vary randomly within specified ranges according to the preference of the operator. Frequency settings above 200 Hz have limited displacement amplitude emission capability, in keeping with clinical safety concerns and the mechanical constraints of the provided system, and are thereby confined to the low millimeter to sub millimeter emission ranges (i.e. as low as about 0.1 mm-2 mm).

The active end of the provided linear stepper motor operatively drives the contacts 12 and 12a of angiogenic percussion device 10 in a substantially linear, reciprocating pathway. The spacing between contact 12 and 12a, as well as the rotation of contact 12a (relative to a skin surface) is electronically controllable by an operator, such as to enable optimized imaging while holding angiogenic percussion device 10 otherwise substantially static. Furthermore, the length of contact 12 and 12a relative to the housing (or casing) of angiogenic percussion device 10 is telescopically controllable (again control not shown), such as to enable subtle angulation of angiogenic percussion device 10 against a skin surface of patient 20 (which assist optimized imaging and targeting) while maintaining balanced contact of the two contact nodes against the chest surface of patient 20. In a variation, a directional control may also be added to the linear stepper motor within the housing of angiogenic percussion device 10, such as to enable subtle controlled or randomized angulation shifts of at least one of the contacts 12 or 12a, and thereby varying directivity of the emitted percussive waveform while an operator holds the device otherwise substantially static.

The selection of peak maximal displacement amplitudes ranging from 0 (oft), 0.1 to 15 mm deflection is provided by an amplitude regulatory mechanism which is incrementally controlled by the operator. The amplitude regulatory mechanism is enabled by the provided linear stepper motor stroke length control. The stroke length control (and all other parameters) are coordinated via commands from a processor within and interface upon angiogenic percussion device 10 (not shown). Angiogenic percussion device 10 is also optionally programmable to enable selectable percussion force (or power) control at a given frequency, as an alternate to (or in addition to) the provided selectable displacement amplitude (or stroke length) control.

Operation of the preferred angiogenic percussion device 10 is as follows. The operator inputs commands, which thereafter sends commands to a processor, located within angiogenic percussion device 10. Commands indicate the operator selection of various signal parameters such as emission frequency, modulation, displacement waveform emission shapes (selectable between sinusoidal, square, exponential, saw tooth and any other programmable wave shape), maximum stroke length (anywhere within the 0.1-15 mm range), and percussion emission according to cardiac phase.

Randomic mode percussion may optionally also be selected, whereby any percussive waveform parameter or pattern may be randomly varied over a specified range.

A fan (not shown) is advantageously disposed within the housing of angiogenic percussion device 10, (as well as a pair of ventilation holes through the housing—also not shown), to assist convective air cooling of the provided linear stepper motor therein, which enables prolonged application times such that the device will not overheat. Alternatively, any other known suitable cooling mechanism may be used. Angiogenic percussion device 10 is also optionally equipped with a controllable heating system for heating the contact surface of contacts 12 and 12a, for added patient comfort.

Angiogenic percussion device 10 is powered by an AC power cord, or as a second means via a portable DC battery pack (not shown), which is slide-ably and removably disposed within the handle of the device (not shown) The DC battery pack is advantageous as it enables operation of angiogenic percussion device 10 in the community (eg. on the bus, while traveling etc) wherein no AC power is commonly available.

It should be emphasized that angiogenic percussion device 10 as herein described comprises a "preferred" means (or apparatus) for the deliverance of angiogenic percussion therapy in the treatment of coronary artery disease, and accordingly may be varied in many ways to enable function of an effective angiogenesis system. In essence, any low frequency non-invasive percussor (or massage vibrator, or impact oscillation device by other name) with an attachment interface suitable to enable direct selected body surface contact, operational to emit or apply percussion in the range of 1-1000 Hz (and optimally within the range of 1-200 Hz), and most preferably via a dual amplitude modulated signal in the 8-15 Hz range and 20-120 Hz range, with a maximum displacement amplitude enablement in the 0.1-15 mm range, which is operable under engagement forces at least 5-10N (and preferably at least 20 N), may be used to provide an effective angiogenesis system.

It should be understood that the choice of a linear stepper motor is not critical to enable angiogenic percussion therapy in the 1-1000 Hz range, and a high powered voice coil, rotorary motor with a rotary to linear conversion element such as a cam or crank may alternatively be employed.

The preferred angiogenic percussion device 10 (and provided variants) is powered by battery or power cord at a range of voltages (e.g. North America—110, 120 V, Europe—220V, Japan 95, 105 V, Australia 240 V) and is (as stated) operable both by battery and power cord for emergency settings.

Detachable non-imaging contacts 12 are provided in a plurality of sizes, (i.e. small, medium and large), and made substantially of silicone rubber, however any resilient yet non-obtrusive material (preferably shaped with a convex contact surface in rib space transthoracic applications), to allow comfortable application against the body of patient 20 may be used. The contacts 12 and 12a are sized to make contact with an intercostal space of the human body, and rest evenly against the upper and lower rib, with an outward convexity (or contour) to ensure soft tissue contact and concentrate angiogenic percussion therapy effectively. Non-imaging contact 12 advantageously comprises a semi spherical dome shape, with a flat planar circular base (the base being of similar size to the head of a stethoscope), wherein the base ranges in size between 2 cm, 3 cm and 4 cm diameter. It should be understood that the exact shape of contacts 12 (i.e. a semi spherical dome) is not critical, and that any shaped contact head may be used, as long as efficient seating within the intercostal spaces of the patient 20 is enabled. Optionally, a variety of contacts comprising suction cups (not shown) are provided to enable an additional active retraction force, provided the patient is not significantly diaphoretic. A soft rubber lining (or more specifically, a vinyl lining with foam rubber underlay of known type) may optionally overly the engagement surface of contacts 12 in order to impart a more comfortable application (which is especially useful for extremely tender skinned females with fleshy breast tissue who often are very sensitive to pressure applications to the chest wall). It should also be understood that the exact size of contacts 12 or 12a is not critical, and a selection of variant contacts (not shown) with even smaller contact surfaces may be used, enabling a direct seating within the rib space of the patient 20 such that the ribs themselves axe minimally or not touched. This manner of chest wall contact provides a more comfortable application for some individuals.

The preferred embodiment for angiogenic percussion therapy in cardiac applications comprises a pair of adjustably spaced contacts 12 and 12a operatively attached to the active end of a linear stepper motor disposed within angiogenic percussion device 10, to provide concentrated therapy (preferably) to either side of sternum at the selected intercostal space as per the prescribed methodology. In a further variation, to optimize sonic penetrability to the ischemic region(s) of the heart and to account for variable location of the heart within the thoracic cavity, a plurality beyond a pair of contacts 12 and 12a may be used. Placement of a plurality beyond a pair of contacts 12 and 12a could be, for example be placed generally lateral to the anatomic right and left sternal border, encompassing any two or all of the $3^{rd}$, $4^{th}$ and $5^{th}$ intercostal spaces. Alternatively, a single contact 12 or 12a may be used.

Referring back to FIG. 1, a perspective view of a the preferred embodiment, a hand held single imaging/treatment probe angiogenic percussion device 10, and method as applied to a patient 20 is shown. This system (as per the preferred "dual function system" described earlier) employs a low frequency angiogenic percussion source—preferably a linear stepper motor, and high frequency ultrasonographic imaging (HFUS) taken together in concert (simultaneously) via a single combined hand held transmission unit, for visually directing low frequency angiogenic percussion therapy within the body of the patient 20. The anatomically leftward oriented contact 12a of the attachment interface of angiogenic percussion device 10 contains an ultrasonic imaging transducer (not shown—located at the active end of angiogenic percussion device, proximate patient 20), whereby a real time multidimensional image can be viewed on ultrasonographic 2-D display 17. The ultrasonic imaging transducer is operatively connected (or acoustically coupled) to a low frequency angiogenic percussion source (also not shown—located within the housing of angiogenic percussion device 10) such that upon activation, when the low frequency angiogenic percussion source generates repetitive reciprocating motion, the ultrasonic imaging transducer oscillates and thereby is enabled to deliver low frequency angiogenic percussion simultaneously (i.e. together in real time) with HFUS imaging, all via a shared contact surface of contact 12a, to the patient 20. An optional weight added within or exterior to the housing of angiogenic percussion device 10 (weight not shown), adds inertia to the system to ergonomically assist the operator (i.e. to apply engagement force) during hand held placement of angiogenic percussion device 10 which is particularly helpful in cardiac or other transthoracic applications. An example of a useful ultrasonic image 18 (in this case an image of septal and posterolateral regions of the heart is depicted), is shown on ultrasonographic 2-D display 17, The angiogenic percussion source of the angiogenic percussion device 10 advantageously enables selectable peak displacement amplitude, frequency and displacement wave form control to generate a series of oscillations with an oscillating speed in the 1-1000 Hz range, and more particularly in a 1-200 Hz range, with both modulated waveform control (i.e. amplitude modulation between two fundamental frequencies), and random and non-random modes. It should be understood however that this particular selection of angiogenic percussion source is not critical to enable use of the preferred dual function system, and any known angiogenic percussion source operable to generate angiogenic palpable percussion within the 1-1000 Hz range (so long as the therapeutic angiogenic percussion wave form does not disable the necessary ultrasonic imaging wave form) may be used, regardless of the level of provided vibratory emission control. Such angiogenic percussion sources may for example comprise but not be limited to; linear stepper motors, linear stepper motors with displacement amplification, rotary stepper motors with a rotary to linear conversion element such as a cam or crank, magnetostrictive actuators, voice coils, shakers (e.g. with or without neodymium magnet transducers), and ceramic servo motors coupled to either a rotary (with cam) or linear stage. The preferred angiogenic percussion source should be operable at broad range of displacement amplitude settings while under load, such as to optimally enable a high energy penetrative system of angiogenic percussion therapy (or impact oscillatory or vibratory therapy by other name) for transthoracic and most particularly coronary angiogenesis applications.

The ultrasonic imaging transducer of angiogenic percussion device 10 is operatively attached to the reciprocating motor (preferably a linear stepper motor) disposed within the housing of angiogenic percussion device 10 (not shown), such that when the active end of the oscillating motor oscillates, the oscillations are linearly (axially) transmitted to the ultrasonic imaging transducer. The ultrasonic imaging transducer, embodied as percussive imaging contact 12a, is removably attachable, and other attachment interfaces, such as a singular, pair or greater than a pair of non-imaging contacts 12 (or any other suitable non imaging contact) may be used.

The preferred ultrasonic imaging transducer for use with the angiogenic percussion device 10 comprises a phased array imaging transducer enabling real time multi-dimension imaging acquisition, preferably 2D imaging acquisition, and optionally real time 3D volume acquisition. Phased array imaging transducers are preferred for cardiac applications as the piezoelectric element configuration and timing of phased arrays enable a relatively small foot print (such as to enable seating in a rib space) while giving rise to a relatively large sector (such as useful to best image the heart). 3D volume acquisition, while much more expensive to implement (and hence not necessarily preferred), is advantageous as an operator can deduce an acoustic window which enables penetration to both the lateral and medial margins of the heart without having to necessarily mechanically rotate the implemented ultrasonic transducer. Real time imaging is preferred so an operator can evaluate LV function and stability of an echocardiographic acoustic window (such as to best maintain the acoustic window) throughout therapy.

It should be understood that while a phased array imaging transducer is preferred, any ultrasonic imaging transducer enabling real time multidimensional imaging (2D or 3D), or even blind or imaging guided Doppler interrogation only, may alternatively be used for the angiogenic percussion device 10 according to the invention. The ultrasonic imaging transducer of percussive imaging contact 12a is preferably disposed within a protective engagement housing (to reduce wear and tear on the engagement face of the transducer, particular at the edges and corners), and is preferably sized and contoured to enable operative seating within a rib space of patient 20 to best enable transthoracic percussion transmission.

While the preferred attachment interface of angiogenic percussion device 10 comprises contact 12 and 12a spaced to enable seating across the sternum of patient 20, in a variation, a variety of attachment interfaces with a plurality of vibratory contacts beyond a pair, spread to enable contact to a plurality or rib spaces either across the sternum and/or to varying rib spaces to either side of the sternum, some containing an ultrasonic imaging transducer and some not, may be used, in any workable configuration.

A variant "multifunction system" is also provided, which in addition to providing a means of transmission for low frequency angiogenic percussion therapy concurrently and simultaneously with ultrasonic imaging via a single transmission instrument (i.e. as above in the preferred "dual function" system), further enables a LFUS treatment wave form emission in the 1 kHz-500 kHz range.

In this variant multifunction system embodiment (which may be used in both coronary and cerebral vasculature applications), non-invasive low frequency angiogenic percussion (i.e. in the sonic to infrasonic range), low frequency treatment ultrasound (in the 1 kHz-500 kHz range), and high frequency ultrasonic imaging are utilized non-destructively in concert (i.e. simultaneously) to provide an optimized therapy system.

The variant multifunction system is generally enabled by a percussive attachment interface which shares an imaging and lower frequency therapeutic ultrasonic emission surface. For example, an ultrasonic imaging transducer, preferably a phased array, may be disposed around or alternatively placed side by side to an incorporated LFUS actuator (or more broadly, an actuator operable to emit oscillations in about the 1 KHz—about 500 KHz range), such that the active ends (or engagement faces) of both units are directly adjacent to one another and thereby sharing a common application surface for contact to the patient 20. Treatment applicators of similar design to this are discussed in U.S. Pat. No. 5,558,092 to Unger et al, as well as U.S. patent application Ser. No. 11/036,386 to the present applicant, incorporated herein by reference. The relative geometry (i.e. ultrasonic imaging transducer disposed about the LFUS transducer (or vice versa) and the relative contact surface areas of the two complimentary engagement faces are not critical, as long as both the active contact surface of the LFUS transducer and the active contact surface of the ultrasonic imaging transducer are represented to a sufficient degree to enable their respective functions, and are placed in close proximity to one another. Preferably the shared contact surface provided would be of a size, and shape, to enable efficient seating in a rib space of the patient 20, to optimize use and angiogenic percussion transmission in transthoracic applications. In a variation, a HFUS ultrasonic imaging transducer may be mounted end to end with a LFUS actuator, whereby the LFUS waveform is transmitted directly through the HFUS ultrasonic imaging transducer.

It should be understood that while the low frequency angiogenic percussion source to the multifunction system also advantageously comprises the active components of preferred angiogenic percussion device 10 (i.e. to enable a high degree of low frequency angiogenic percussion control), this selection of low frequency angiogenic percussion source is not critical to enable use of the variant multi function system according to the invention, and any known angiogenic percussion source operable to generate angiogenic percussion within the 1-1000 Hz range (so long as the therapeutic wave form does not disable or significantly interfere with the necessary ultrasonic imaging wave form, or therapeutic low frequency ultrasonic wave form, or more broadly waveform in the 1 KHz-500 kHz range) may be used, regardless of the level of provided vibratory emission control. Such angiogenic percussion sources may for example comprise, but not be limited to: linear stepper motors, linear stepper motors with displacement amplification, ceramic servo motors coupled to either a rotary (with cam) or linear stage, rotary motors with rotary to linear conversion elements, magnetostrictive linear motors, voice coils, and shakers (e.g. with or without neodymium magnet transducers), and asymmetrical eccentrically spinning or agitated weights.

In the preferred embodiment, (which utilizes low frequency angiogenic percussion solely in the palpable sonic to infrasonic ranges), angiogenic percussion device 10 is secured to patient 20 by the hand or hands of an operator, wherein an alternative means of engagement employs use of clamp or a belt (neither shown).

In implementation of angiogenic percussion timed to the diastole of a cardiac cycle, angiogenic percussion device 10 (or variant) further comprises a processor and ECG sensor (preferably a five lead system—not shown) utilized to determine the start of ventricular systole (by sensing of a QRS complex), where after a pre-programmed and optionally rate modulated delay (approximating the length of ventricular systole) is implemented, where after angiogenic percussion is initiated and maintained until the onset of the next sensed QRS complex. Further, the operator, upon viewing an ECG display monitor with interpolated percussion emission display (not shown), can adjust (or fine tune) the timing of angiogenic percussion emission. In essence the cardiac phase controlled angiogenic percussion delivery system preferably comprises a blended technology of a angiogenic percussion source and known intra-aortic balloon pump diastolic timing technology, of which the company ARROW inc., is an exemplary supplier.

Ideally diastolic timed angiogenic percussion should generally commence from the terminal end of the T wave, and then discontinue upon the onset of the deflection of the QRS complex as visualized by a provided ECG trace waveform. As stated the use of the diastolic timed angiogenic percussion is of significant importance when the patient 20 is suffering from a weakened ventricle which may deteriorate to a state of heart failure during continuously applied (i.e. without a identifiable break in cadence definable in relation to the cardiac cycle) angiogenic percussion therapy.

The preferred method of employment of the angiogenic percussion device 10 for treatment of arterial disease comprises the step of applying angiogenic percussion to a selected or pre-determined external body surface deemed generally proximate the ischemic zone, and there after locating an optimized position for angiogenic percussion device 10 and maintaining said position by ultrasonic imaging of a target by direct visualization or by anatomic reference via the preferred angiogenic percussion device 10 (or other suitable percussion device as described above).

A provisional step of employing diastolic timed angiogenic percussion via the cardiac phase controlled angiogenic percussion delivery system (or any suitable variation thereof) in the special case wherein the patient 20 deteriorates into a state of hemodynamic compromise during angiogenic percussion therapy, is also provided according to the invention. Diastolic timed angiogenic percussion reduces LV diastolic pressures, promotes LV diastolic filling, and promotes a positive inotropic effect to LV function by Starling's Law, and also is known to increase coronary flow in narrowed coronary arteries. It should be understood that diastolic timed percussion may alternatively be employed throughout the course of angiogenic percussion therapy, at the discretion of the clinician.

It is preferred, that angiogenic percussion applied "continuously" throughout the cardiac cycle, including systolic period) if tolerated by patient 20, such as to maximize endothelial stimulation and thereby with greater efficiency enhance or induce coronary angiogenesis.

In reference again to FIG. 1, the preferred dual function imaging—targeting method comprises the step of applying and directing angiogenic percussion by means of ultrasonic imaging (i.e. the angiogenic percussion device 10 applied to patient 20 is shown), however any suitable variant angiogenic percussion device—as described above—coupled to an ultrasonic imaging transducer at its active end may be used. The angiogenic percussion device 10 (or variation thereof is optimally placed and directed via ultrasonic imaging, to emit angiogenic percussion towards an ischemic region (or vasculature) targeted. This is accomplished by either direct visualization or by anatomic reference. Again, the second optional provisional step of employing diastolic timed angiogenic percussion via the cardiac phase controlled angiogenic percussion delivery system (or suitable variation thereof) in the special case wherein the patient 20 deteriorates or presents into a state of hemodynamic compromise may be used. Again it should be understood that angiogenic percussion therapy directed by ultrasonic imaging may be utilized with diastolic timed percussion throughout the course of therapy regardless of the physiologic status of patient 20.

In a prophized application of angiogenic percussion device 10 in a clinical application, a patient with known CAD, wherein options of percutaneous coronary intervention or bypass surgery have been exhausted, presents to the Cardiology clinic for transthoracic angiogenic percussion therapy is herein described.

A 62 year old male with class 4 angina with known reversible ischemia to the anteroseptal wall by Persantine MPI presents to the cardiac clinic for chest wall percussion angiogenic therapy. The patient has had numerous repeat stents and coronary artery bypass surgery to a diffusely narrowed Left Anterior Descending Artery, and further angioplasty and surgery on this vessel are no longer an option according to the patient's Cardiologist. The patient uses nitro spray usually at least 4 times/day, for the most minimal exertion such as walking slowly on a flat incline. The patient reportedly can walk only 2 minutes on the Bruce Protocol before experiencing moderate angina, and 2 mm of flat ST depression in the anterior leads.

The patient is greeted by a cardio-echo technician, and is escorted and placed supine, upon on a stretcher with a pillow placed behind his head. An intravenously line is started, and the patient is monitored by ECG, O2 Sats, and non-invasive blood pressure cuff. Crash Cart and emergency drug tray available.

The attending Cardiologist reviews the MIBI and Cath report such as to determine the zone of ischemia, in this patients case the anteroseptal wall.

Cardio-echo technician applies the pair of contacts 12 and 12a of angiogenic percussion device 10 over the sternum (with ultrasonic conduction gel), and identifies a parasternal echocardiographic window upon the chest wall which generally depicts the rib space and acoustic pathway to the identified ischemic zone (in this case the anteroseptal wall). The left third, fourth or fifth intercostal space is considered with the transducer held close to a 90 degree (plus or minus 10 degrees) angle with respect to the chest wall surface (which best accommodates the angiogenic percussion device 10). The ribspace and chest wall position comprising the smallest chest wall to anteroseptal wall distance is selected—for this patient a good parasternal long axis view is established showing the anteroseptal wall at the left fourth intercostal space, with the anatomically leftward contact 12a placed about 2 cm lateral from the sternal margin (with ultrasonic image present during both phases of normal respiration).

The cardio-echo technician turns on angiogenic percussion device 10 at a low initial peak amplitude (0.1 to 1 mm displacement) and thereafter gradually titrates the displacement amplitude upwards to a tolerance (comfort) level of the patient. The weight of the angiogenic percussion device (comprising about 20 newtons of engagement force) is used, and angiogenic percussion is gently increased in amplitude to a peak of 4 mm, which corresponded to the patient maximum described tolerance. A modulated percussive waveform with a base frequency of 8 Hz, modulated upon a 80 Hz carrier wave is selected to match the resonance frequency of the heart and epimyocardium within the thoracic cavity to maximize internal agitate effect. Angiogenic percussion therapy continues for a 20 minute treatment session with ECG (ST segments), BP and O2 sats monitored. The echocardiographic window is monitored by both the cardio echo-technician and the patient. The patient assists by transiently holding the angiogenic percussion device in place and periodically applies extra engagement force when feeling up to it.

At ten minutes into the therapy session the cardio-echo technician notes that the blood pressure of the patient has dropped below 100 mmHg systolic, so diastolic timed angiogenic percussion is employed, whereby the patient's blood pressure quickly stabilized at 125 mmHg systolic.

The patient completes therapy, IV line and monitoring equipment are detached and patient is discharged. The patient is instructed to present for continuing therapy three four times per week (every second day).

Follow up on the patient after three months shows the following:

1) Repeat MPI shows improvement to previously ischemic anteroseptum region.
2) CCS class of angina improved fro class 4 to 1.
3) Exercise tolerance improves—patient can exercise without chest pain or undue fatigue on 6 minutes via the Bruce Protocol (vs. 2 minutes previously). ST segment depression of 1 mm appears only at end of 6 minutes on the treadmill (vs. 2 minutes previously).
4) Repeat Cardiac Catheterization demonstrates new blood vessel growth by way of collaterals to anterospetal region with improved blush scale.

Figure 6:
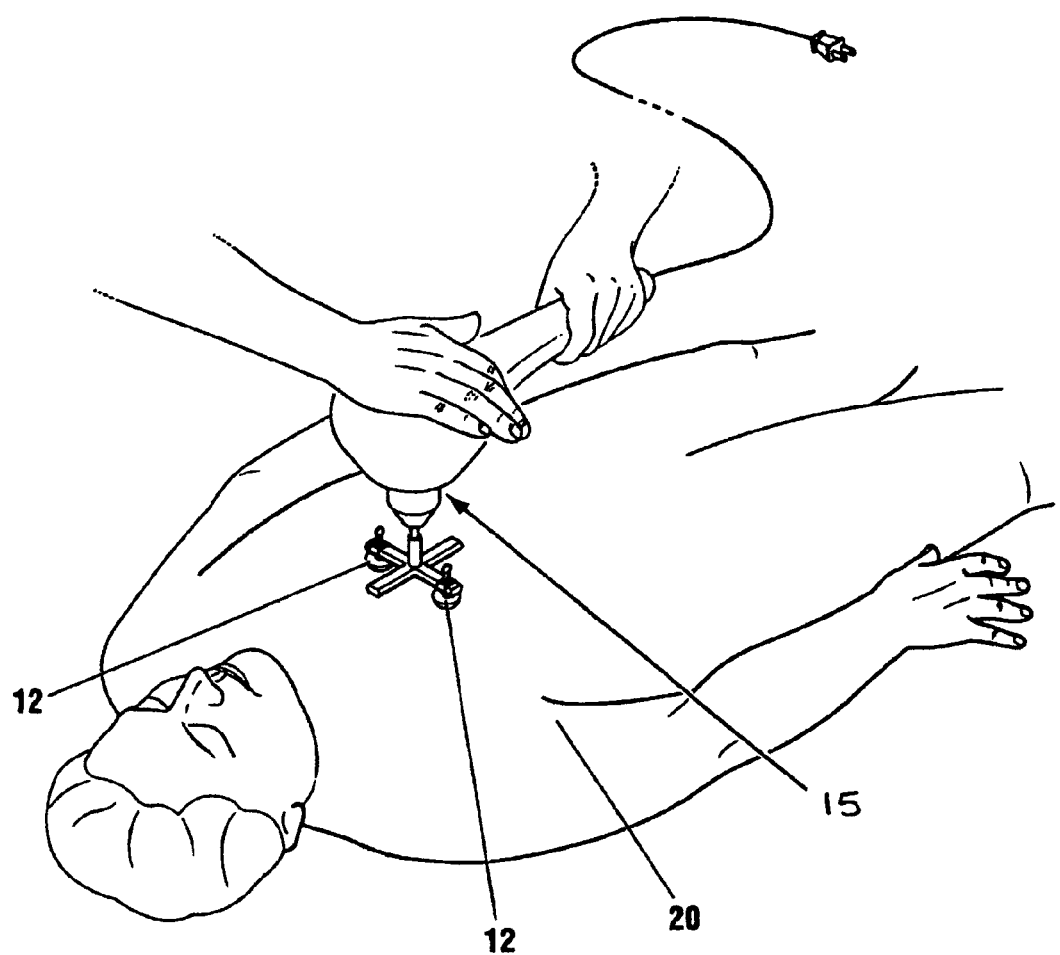
FIG. 6 is a perspective view of a variant angiogenic percussion device without ultrasonic imaging for causing coronary angiogenesis according to the invention, such as for use at home or in an office.

Non-invasive localized angiogenic percussive therapy, such as for coronary, peripheral or cerebral angiogenisis, may also be applied by a patient or family member at home or other non-medically related location. In reference to FIG. 6, engagement to the anterior chest wall bridging the sternum is shown via a variant angiogenic percussion device 15 with a pair of non-imaging contacts 12 (which is preferred in coronary angiogenesis applications performed at home such as by patient self administration). Alternatively, the upper backside of the patient—particular for known cases of posterior wall ischemia—and other areas upon the chest wall may also be utilized. Ideally, for transthoracic cardiac applications whether at home or at a medical clinic, the highest peak force or displacement amplitude deemed safe and tolerable to the patient 20 is preferably selected to ensure optimal penetration and effectiveness of the percussive signal. A plurality greater than a pair of contacts 12 placed to a plurality of differing rib spaces (such as along any two of the $3^{rd}$, $4^{th}$, and $5^{th}$ sternal border—not shown), preferably to either side of the sternum or alternatively exclusively anatomically leftward to the sternum, may alternatively be utilized in these cases as the patient 20 would be unlikely to have the skill to apply ultrasonic imaging to enable targeting of the therapy.

Many modifications are possible to the angiogenesis percussion system without departing from the spirit or innovative concept of the invention.

With regards to the angiogenic percussion source of preferred angiogenic percussion device 10, while the embodiment shown advantageously employs an electromechanical transducer comprising a linear stepper motor (such as to enable a high level of vibratory control), alternatively any known (or adaptable) low frequency (i.e. 1-1000 Hz, preferably at least 8 Hz, more preferably at least 20 Hz) angiogenic percussion device (or impact vibration massage or oscillation device by other name), with a suitable attachment interface for selected body surface contact (preferably contoured and sized to enable concentrated delivery of angiogenic percussion between the rib space or spaces of the patient 20), being operable at a palpable displacement amplitude range of about 0.1-15 mm (preferably at least 1 mm), and engagement forces of preferably >20 Newtons, may alternatively be used, regardless of the level of operator enabled angiogenic percussion control.

Also, while preferred angiogenic percussion device 10 comprises a hand held device sized to enable hand held operation, engagement and maneuverability, alternatively an angiogenic percussion source of comparable emission capacity may be fixed in place as part of a chair or bed which could be particularly useful for angiogenic percussion to the upper backside of the patient 20, such as in treatment of cardiac ischemia, or if applied to the posterior—posterolateral region of the neck for treatment of cerebral vasculature ischemia.

Furthermore, while the preferred embodiment (apparatus) discloses a single motor located within angiogenic percussion device 10, a pair or a plurality of beyond a pair of motors may also be used (for example, one motor for each contact 12 or 12a).

It should also be noted that there is effectively no definable maximal nor minimal limit to displacement amplitude range or engagement force applied in angiogenic percussion therapy (i.e. the intensity emitted is generally a function of the tolerance of the patient 20 which will vary markedly). Any of the above variations to angiogenic percussion source may be therefore adapted in size and scale to enable angiogenic percussion at higher or conversely lower loads and displacement amplitudes than what is otherwise disclosed according to the invention. For example, while the preferred embodiment shown (i.e. angiogenic percussion device 10) provides a peak displacement amplitude capability of up to 15 mm, this enablement is generally in excess of what is typically required, and a device limited to lower peak displacement amplitudes (i.e. with an upper limit as low as about 4-8 mm), may alternatively be employed for transthoracic cardiac applications, and lower peak displacement amplitude levels of up to about 2 mm may be satisfactory for other applications to other body parts requiring angiogenesis, such as cerebral vasculature applications. Lower peak displacement amplitude devices are potentially "safer" (i.e. as the "tolerance" level of the patient 20 may be difficult to judge at the time of treatment), and confer lighter weight more compact systems, which are generally easier to manoeuvre and operate by hand. In an exemplary alternative embodiment, the vibrator employed may be operable to the maximum displacement amplitude allowable (i.e. deemed safe) under the officiating governmental regulatory body or bodies of the country wherein the angiogenic percussion device is to be commercialized.

With regards to the preferred attachment interface, while the embodiment shown incorporates a pair of contacts 12 and 12a spaced to enable bridging the sternum of patient 20, any other attachment interface suitable to enable human contact could potentially be used according to the invention, such as by way of example only; suction cups, a single contact 12 or 12a, a plurality beyond a pair of contacts 12 or 12a enabling contact with a plurality or rib spaces, and variant contacts enabling HFUS ultrasonic imaging with or without LFUS wave form emissions in the 1-500 kHz range), which may be utilized solely, or in any combination, as per the methods described, to best suit the clinical situation and/or preference of the operator. An attachment interface comprising a LFUS transducer or more broadly a therapeutic actuator operable to emit oscillations in the 1 KHz-500 KHz range may also be employed without an ultrasonic imaging transducer or Doppler transducer.

It is also possible to utilize more than one angiogenic percussion source for placement to a plurality of locations along the body of the patient 20, such as to further ensure maximal penetration and effectiveness of angiogenic percussion therapy for treatment of coronary artery disease. In this alternative embodiment the angiogenic percussion devices should optimally be operated in phase to one another (i.e. to avoid potential destructive interference of the therapeutic signal), and may optionally be strategically operated at differing frequencies, such as a lower frequency to match the resonance frequency of the organ (such as the heart) and a higher frequency to match the resonance frequency of the tissue of the organ (such as the epimyocardium of the heart). This technique may be of particular relevance wherein an imaging technique to direct angiogenic percussion therapy is not employed.

It should be understood that while the preferred embodiment of the present invention involves the administration of non-invasive localized percussion for causing or inducing "angiogenesis" (growth of "new" blood vessels), the apparatus and methods disclosed are equivalently useful for enhancing the development or growth of collaterals which are generally defined as pre-existing (as opposed to strictly "new") tiny dormant arteries/arterioles or capillaries which typically bypass arterial narrowings. The concepts of angiogenesis and improving growth of collaterals are often deemed equivalent to those skilled in the art, as both are deemed growth and development of arterial vasculature as opposed to correction of vasculature. Therefore, in its broadest sense the present invention and all the variations of application of vibro-percussion incorporated herein are useful for inducing growth of arterial blood vessels, including epicardial, cerebral, or peripheral arteries, including their respective arterioles, capillaries and collaterals.

Thereby, the present invention embodies a method for developing collateral circulation (e.g. coronaries), comprising the step of applying transcutaneous vibration at an impact frequency in the range of 1-1000 Hz, and an amplitude in the range of 0.1-15 mm to an external body surface (e.g. upper torso) deemed to generally overly a diseased arterial vasculature of an ischemic area in need of collateralization, whereby the forces of the percussions provided penetrate from said body surface to said diseased vasculature, to cause development of collaterals within said diseased vasculature.

Furthermore, while the preferred embodiment of the present invention involves the administration of non-invasive, preferably localized percussion for causing or inducing arterial growth, the apparatus and methods disclosed could easily be useful for emergency arterial thrombolysis applications.

As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims.

I claim:

1. A non-invasive method for inducing growth of coronary arterial blood vessels, comprising the steps of:
    providing means for delivering percussion upon an external body surface of an individual with a waveform and serial impact frequency in the range of 1 Hz to 200 Hz, and a displacement amplitude in the range of 1 mm-15 mm, and
    applying a series of consecutive, localized percussions at a waveform and serial impact frequency in the range of 1-200 cycles per second and a displacement amplitude in the range of 1 mm-15 mm, to an external body surface deemed to overlie a diseased coronary arterial vasculature supplying a heart in need of growth of coronary arterial blood vessels, whereby forces of said series of consecutive, localized percussions penetrate from said external body surface to said diseased coronary arterial vasculature, such as to induce growth of coronary arterial blood vessels within said diseased coronary arterial vasculature,
    wherein said means for delivering percussion comprises at least one contact node adapted to enable operative seating against at least one of a chest wall and an upper back external body surface of a patient receiving said series of consecutive percussions from said means for delivering percussion, wherein said contact node delivers said series of consecutive percussions.

2. The method of claim 1, wherein said series of consecutive, localized percussions are applied at a displacement amplitude of at least 4 mm.

3. The method of claim 1, wherein said series of consecutive, localized percussions are applied at a frequency of at least 8 impacts per second.

4. The method of claim 1, wherein said series of consecutive, localized percussions are delivered via a vibratory waveform comprising a first lower frequency modulated upon a second higher frequency, whereby said first and second frequencies lie in a range of frequencies consistent with a cardiac related resonance frequency.

5. The method of claim 2, wherein said external body surface comprises the upper back of a patient receiving said series of consecutive, localized percussions.

6. The method of claim 1, further comprising the step of selectively limiting said percussions during a systole of said patient.

7. A method for inducing growth of coronary blood vessels, comprising the steps of:
   a) providing means for delivering percussion comprising a percussion device operable to deliver mechanical oscillations with a waveform and serial impact frequency in the range of 1 Hz to 200 Hz, and
   b) delivering a series of consecutive percussions at a frequency in the range of 1-200 Hz and a displacement amplitude in the range of 1 mm-15 mm via said percussion device locally upon an upper torso overlying the thoracic cavity of a patient in need of growth of coronary blood vessels, whereby said series of consecutive percussions penetrate to a diseased coronary vasculature such as to induce growth of coronary blood vessels,
   wherein said percussion device has at least one contact node adapted to enable operative seating against at least one of a chest wall and upper back of said upper torso of said patient receiving said series of consecutive percussions from said percussion device, and wherein said contact node delivers said series of consecutive percussions.

8. The method of claim 7, wherein said series of consecutive percussions are applied at a displacement amplitude of at least 2 mm.

9. The method of claim 7 wherein said series of consecutive percussions are applied with a repetitive impact frequency of at least 20 impacts per second.

10. The method of claim 7, wherein said at least one contact node is adapted to enable operative seating within a rib space of said patient.

11. The method of claim 7, wherein said percussion device has at least a pair of contact nodes spaced to enable seating across a sternum of said patient receiving said series of consecutive percussions from said percussion device, wherein said contact nodes jointly deliver said series of consecutive percussions.

12. The method of claim 7, wherein said percussion device has a plurality of contact nodes spaced to enable seating upon a plurality of rib spaces at differing intercostal space levels of said patient receiving said series of consecutive percussions from said percussion device, wherein said plurality of contact nodes jointly deliver said series of consecutive percussions.

13. The method of claim 7, wherein said percussion device has at least one percussive contact comprising an ultrasonic imaging transducer, whereby said ultrasonic imaging transducer delivers said series of consecutive percussions from said percussion device to said upper torso, thereby enabling targeting of said series of consecutive percussions via a real time image produced on an ultrasonic display.

14. The method of claim 7, wherein said series of consecutive percussions are applied at a displacement amplitude of at least 4 mm.

15. The method of claim 7, wherein said growth of coronary blood vessels comprises at least one of growth of new coronary blood vessels, and growth of pre-existing collaterals.

16. The method of claim 7, wherein said series of consecutive percussions are selectively limited during at least a portion of a systole of the cardiac cycle of said patient receiving percussion from said percussion device.

17. The method of claim 7, further comprising the step of manually applying an engagement force upon said percussion device during delivery of said series of consecutive percussions operable to provide therapeutic penetration of said series of consecutive percussions to within said thoracic cavity.

18. The method of claim 7, wherein said percussions are applied to at the said upper back of said patient receiving said series of consecutive percussions from said percussion device.

19. A non-invasive method for inducing coronary arterial growth comprising the steps of:
   a) providing means for delivering percussion comprising a hand held percussion device operable to deliver low frequency infrasonic to sonic mechanical percussion with a waveform and serial impact frequency in the 1-200 Hz range and a stroke length in the 1 mm to 15 mm range,
   b) engaging said percussion device to an upper torso overlying the thoracic cavity of an individual in need of coronary arterial growth,
   c) delivering said percussion via said percussion device to said upper torso while manually controlling an engagement force of said percussion device against said upper torso by the hand of an operator, and
   d) inspecting for evidence of transmission of said percussion within said individual to confirm satisfactory engagement of said percussion device, whereby said percussion penetrates to the coronary vasculature of said patient such as to induce coronary arterial growth
   wherein said hand held percussion device comprises at least one contact node adapted to enable operative seating within a rib space on said upper torso overlying the thoracic cavity of said patient receiving said percussion from said percussion device, wherein said contact node delivers said percussion.

20. A method for inducing growth of coronary blood vessels, comprising the steps of:
   providing means for delivering percussion comprising a percussion device operable to deliver percussion with a waveform and serial impact frequency in the 1 Hz to 200 Hz range;
   non-invasively applying said percussion with a palpable displacement amplitude in the range of 1 mm to 15 mm locally upon an upper torso overlying the thoracic cavity of a patient having a diseased coronary vasculature in need of growth of coronary blood vessels, wherein the forces of said percussion penetrate to said diseased coronary vasculature, such as to induce growth of coronary blood vessels within said diseased coronary vasculature; and
   wherein said percussion device comprises at least one contact node adapted to enable operative seating within a rib space on said upper torso overlying the thoracic cavity of said patient receiving said percussion from said percussion device, wherein said contact node delivers said percussion.

21. The method of claim 20, wherein said percussion has a displacement amplitude of at least 2 mm, and is applied locally to at least one of a chest wall and upper back of a patient receiving said percussion.

22. The method of claim 21, wherein said percussion is applied with an impact frequency of at least 20 impacts per second.

23. A method for inducing neo-coronary arterial growth comprising the steps of:
   providing a means for delivering non-invasive localized transthoracic vibration with a waveform and serial impact frequency in the range of 8 Hz to 120 Hz, and a stroke length within the range of 1 mm to 15 mm, and applying said vibration locally to at least one of a chest wall and upper back of an individual receiving said vibration, wherein the emissions of said vibration are selectively limited during a systole of the cardiac cycle of said individual, and wherein said means for delivering localized transthoracic vibration comprises at least one contact adapted to enable operative, localized seating against at least one of a chest wall and upper back of said individual receiving said vibration, wherein said contact delivers said vibration.

24. The method of claim 23, wherein said vibration is applied repeatedly at an impact frequency of at least 20 cycles per second.

25. The method of claim 23, wherein said vibration is emitted in a randomized manner.

* * * * *